(12) United States Patent
Py

(10) Patent No.: US 9,801,787 B2
(45) Date of Patent: Oct. 31, 2017

(54) MULTIPLE DOSE VIAL AND METHOD

(71) Applicant: Daniel Py, Larchmont, NY (US)

(72) Inventor: Daniel Py, Larchmont, NY (US)

(73) Assignee: DR. PY INSTITUTE LLC, New Milford, CT (US)

( * ) Notice: Subject to any disclaimer, the term of this patent is extended or adjusted under 35 U.S.C. 154(b) by 969 days.

(21) Appl. No.: 13/744,379

(22) Filed: Jan. 17, 2013

(65) Prior Publication Data
US 2013/0180618 A1    Jul. 18, 2013

Related U.S. Application Data

(60) Provisional application No. 61/587,525, filed on Jan. 17, 2012.

(51) Int. Cl.
*A61J 1/20* (2006.01)
*A61J 1/14* (2006.01)
(Continued)

(52) U.S. Cl.
CPC .............. *A61J 1/2096* (2013.01); *A61J 1/10* (2013.01); *A61J 1/1406* (2013.01); *A61J 1/1475* (2013.01); *A61M 39/24* (2013.01); *A61J 1/22* (2013.01)

(58) Field of Classification Search
CPC .............. B65D 47/205; B65D 47/2031; B65D 47/2037; B65D 47/2043; A61J 1/2037;
(Continued)

(56) References Cited

U.S. PATENT DOCUMENTS 1,708,060 A * 4/1929 Harrison ............... F16K 27/003
137/269
1,967,439 A * 7/1934 Heineman ............. A61J 1/2096
141/329
(Continued)

FOREIGN PATENT DOCUMENTS

EP    0748635 A2    12/1996
FR    2929248 A1 * 10/2009 ........... A61J 1/1412
(Continued)

OTHER PUBLICATIONS

Supplementary European Search Report for European Patent Application No. 13738633.0, issued on May 5, 2015. 7 pages.
(Continued)

*Primary Examiner* — Timothy L Maust
*Assistant Examiner* — Andrew StClair
(74) *Attorney, Agent, or Firm* — McCarter & English, LLP

(57) ABSTRACT

A vial for storing multiple doses of a substance to be dispensed into one or more syringes or other delivery devices. The vial has a body, a variable-volume storage chamber within the body for storing multiple doses of the substance therein, and a one-way valve connectable in fluid communication with a syringe or other delivery device. The one-way valve is moveable relative to the body between first and second positions (i) one of which permits the valve to open so that substance from the variable-volume storage chamber can flow therethrough and into the syringe or other delivery device connected in fluid communication therewith, and (ii) one of which prevents the valve from opening.

58 Claims, 16 Drawing Sheets

(51) Int. Cl.
*A61M 39/24* (2006.01)
*A61J 1/10* (2006.01)
*A61J 1/22* (2006.01)

(58) Field of Classification Search
CPC ...... A61J 1/2096; A61J 1/2051; A61J 1/2062; A61J 1/10; A61J 1/22; A61J 1/1406; A61J 1/1475; B65B 1/04; A61M 39/22; A61M 39/24; A61M 2039/242; A61M 2039/2433
USPC .............. 251/82, 89–116; 137/852, 854, 526
See application file for complete search history.

(56) References Cited

U.S. PATENT DOCUMENTS

| | | | | |
|---|---|---|---|---|
| 3,853,157 | A * | 12/1974 | Madaio | A61M 5/1782 |
| | | | | 141/2 |
| 4,493,348 | A * | 1/1985 | Lemmons | A61J 1/2096 |
| | | | | 138/109 |
| 4,862,918 | A * | 9/1989 | Schroeder | B67D 7/0294 |
| | | | | 137/614.19 |
| 5,024,355 | A | 6/1991 | Jouillat et al. | |
| 5,060,704 | A | 10/1991 | Rohrbough | |
| 6,234,363 | B1 * | 5/2001 | Stradella | B65D 47/2037 |
| | | | | 222/148 |
| 6,662,977 | B2 * | 12/2003 | Gerber | B65D 47/205 |
| | | | | 222/494 |
| 7,077,176 | B2 * | 7/2006 | Py | A61J 1/18 |
| | | | | 141/301 |
| 7,175,615 | B2 * | 2/2007 | Hanly | A61J 1/10 |
| | | | | 383/41 |
| 7,226,231 | B2 | 6/2007 | Py et al. | |
| 7,335,186 | B2 | 2/2008 | O'Neil | |
| 7,780,023 | B2 * | 8/2010 | Py | A61J 1/1406 |
| | | | | 215/11.1 |
| 7,810,677 | B2 | 10/2010 | Py et al. | |
| 7,886,937 | B2 | 2/2011 | Py | |
| 2002/0189684 | A1 * | 12/2002 | Williamson | A47G 21/185 |
| | | | | 137/510 |
| 2004/0171993 | A1 * | 9/2004 | Bonaldo | A61M 39/26 |
| | | | | 604/248 |
| 2004/0222224 | A1 | 11/2004 | Plester | |
| 2005/0178462 | A1 * | 8/2005 | Py | A61J 1/1412 |
| | | | | 141/2 |
| 2006/0065677 | A1 | 3/2006 | Py et al. | |
| 2007/0251591 | A1 * | 11/2007 | Kiehne | A61M 39/26 |
| | | | | 137/844 |
| 2008/0221547 | A1 * | 9/2008 | Monty | A61J 1/2096 |
| | | | | 604/500 |
| 2010/0004619 | A1 * | 1/2010 | Rondeau | F16L 37/0985 |
| | | | | 604/407 |
| 2010/0049160 | A1 * | 2/2010 | Jepson | A61J 1/1475 |
| | | | | 604/415 |
| 2010/0140290 | A1 | 6/2010 | Py | |
| 2011/0024463 | A1 | 2/2011 | Py et al. | |
| 2011/0112501 | A1 * | 5/2011 | Garfield | A61J 1/2096 |
| | | | | 604/407 |
| 2011/0272033 | A1 * | 11/2011 | Py | F16K 15/142 |
| | | | | 137/1 |

FOREIGN PATENT DOCUMENTS

| | | |
|---|---|---|
| WO | 9640332 A1 | 12/1996 |
| WO | 2005072427 A2 | 8/2005 |
| WO | 2006037112 A2 | 4/2006 |

OTHER PUBLICATIONS

International Search Report and Written Opinion of the International Searching Authority for International Application No. PCT/US13/21998, mailed Jun. 14, 2013.

* cited by examiner

MULTIPLE DOSE VIAL AND METHOD

CROSS-REFERENCE TO RELATED APPLICATION

This patent application claims benefit under 35 U.S.C. §119 to similarly-titled U.S. Provisional Patent Application No. 61/587,525, filed Jan. 17, 2012, which is hereby incorporated by reference in its entirety as part of the present disclosure.

SUMMARY OF THE INVENTION

The present invention relates to fluid storage and dispensing devices, such as vials, and more particularly, to such devices for storing multiple doses of the substances to be dispensed.

BACKGROUND INFORMATION

A typical vial, such as a medicament vial, includes a vial body defining a chamber for storing a substance to be dispensed, such as a medicament, and a needle-penetrable stopper received within a mouth of the vial body that seals the medicament or other substance within the chamber. In order to withdraw the substance from the vial, the following steps are typically performed. First, the physician or the nurse must fill the syringe with air, and such air, particularly from a hospital, is not sterile. Second, the stopper must be pierced with the syringe needle in order to place the needle tip in fluid communication with the vial chamber. Third, the non-sterile air from the syringe is injected into the vial with enough pressure for the compressed air to replace the volume of liquid pulled into the syringe. Fourth, the vial is put upside down, with the syringe needle vertically beneath the vial, for the liquid of the vial to be drained from the open end of the needle. Then, the plunger of the syringe is pulled vertically downward to, in turn, draw the liquid into the syringe through the immerged tip of the needle in the upside-down vial. Once the syringe is filled, if air has been drawn into the syringe, it is forced out by pushing the plunger with the syringe in the upside-down position in order to eject any air up to the first drop of liquid pushed into the syringe needle. Then, the syringe is used to inject the withdrawn medicament or other substance into, or to otherwise administer it to, a patient.

One of the drawbacks of such a typical known vial is that each time the stopper is pierced with a syringe needle to withdraw a dose of medicament or other substance, the syringe has to be pre-filled with contaminated air from the environment. The needle also can accidentally contact the fingers of the medical personnel or other contaminated surfaces and, as a result, introduce more germs, bacteria or other contaminants into the vial chamber.

A second drawback is that the air injected during previous withdrawals from a multiple dose vial can lead to the reproduction of germs initially contained in the air and injected into the vial. The first withdrawal of the liquid out of a multiple dose vial may be contaminated by the ambient air initially injected into the vial as described above, but between the air injection into the vial and the withdrawal of the liquid, there is not enough time for the germs contained in the air to reproduce in many colonies. However, it can be increasingly dangerous to withdraw liquid from that vial when the amount of dose already withdrawn has been in contact with the germs of previous injections of air into the vial. Accordingly, such vials cannot be safely used to dispense multiple doses of the medicament or other substance without risk of contaminating the substance remaining within the vial chamber after multiple doses have been withdrawn.

A third drawback of the traditional method is that the needle may accidentally stick the skin of the medical personnel, and as a result, may transfer to the patients, contaminants from the blood of the medical personnel, such as hepatitis, a professional disease of medical personnel in general, AIDS, or other ailments.

Yet another drawback is due to the needle transfer when medical personnel withdraw the needle from the vial after the syringe has been filled. At that time the finger of the physician or nurse can be accidentally stuck by the needle and thereby infected with a product contaminated by germ growth in the multiple dose container.

SUMMARY OF THE INVENTION

It is an object of the present invention to overcome one or more of the above-described drawbacks and/or disadvantages of the prior art. In accordance with a first aspect, a device for storing multiple doses of a substance to be dispensed into one or more syringes or other delivery devices comprises a body, a storage chamber within the body for storing multiple doses of the substance therein; and a valve, such as a one-way valve, connectable in fluid communication with a syringe or other delivery device and moveable between first and second positions, and having a closed position preventing substance from passing therethrough and an open position permitting substance to pass therethrough. In the first position the one-way valve is prevented from opening into the open position and substance from the storage chamber cannot pass therethrough, and in the second position the one-way valve is permitted to open into the open position so that the one-way valve permits substance from the storage chamber to flow therethrough and into the syringe or other delivery device connected in fluid communication therewith.

In some embodiments, the one-way valve is configured to substantially prevent any fluid flow in a substantially opposite direction, from the syringe or other delivery device, therethrough, and into the storage chamber.

In some embodiments, the one-way valve includes an elastic valve member defining a normally closed, valve seam that substantially prevents the passage of fluid therethrough when a pressure differential across the valve is less than a valve opening pressure, and allows the passage of fluid therethrough when a pressure differential across the valve exceeds the valve opening pressure. In some such embodiments, the one-way valve includes a valve seat, and the elastic valve member engages the valve seat and forms the valve seam therebetween. In some such embodiments, (i) the elastic valve member defines a progressively decreasing wall thickness in a direction from an inlet toward an outlet of the valve seam, and/or (ii) the valve seat defines a progressively increasing width or diameter in a direction from an inlet toward an outlet of the valve seam.

In some embodiments, the device includes a penetrable and resealable portion or septum that is penetrable by a needle, filling or injection member for filling the storage chamber with substance to be dispensed, and is resealable to hermetically seal a resulting penetration aperture in the septum. In some such embodiments, the septum is resealable by a liquid sealant, radiation, and/or the application of thermal energy thereto.

In some embodiments, the one-way valve is normally biased in a direction from the second position toward the first position. In some such embodiments, the device includes a spring that normally biases the one-way valve in the direction from the second position toward the first position. In some embodiments, the spring is an elastic spring, such as an approximately dome-shaped spring or an approximately bellows-shaped spring.

In some embodiments, (i) in the first position, the one-way valve is engaged with a surface of the device that substantially prevents the one-way valve from opening into the open position, and (ii) in the second position, the one-way valve is sufficiently disengaged from the surface of the device to permit the valve to open into the open position. In some embodiments, the one-way valve includes a valve seat and a valve member normally engaging the valve seat to define the closed position, the valve member being movable relative to the valve seat when a pressure differential across the one-way valve exceeds a valve opening pressure thereof. In the first position, the surface of the device substantially prevents movement of the valve member relative to the valve seat. In the second position, the valve member is sufficiently disengaged from the surface to permit movement of the valve member relative to the valve seat. In some such embodiments, the surface of the vial engageable with the valve member extends substantially annularly about the valve member.

Some embodiments further comprise a connector located adjacent (e.g., downstream) to an outlet of the one-way valve. The connector is adapted to connect thereto the syringe or other delivery device. In some embodiments, the connector is a Luer connector. In some embodiments, connection of the syringe or other delivery device to the connector causes the valve to move in the direction from the first position to the second position. In some such embodiments, the connector defines a surface of the vial engageable with the valve member in the first position to prevent valve opening. In some embodiments, the one-way valve includes a valve seat, and the syringe or other delivery device engages the valve seat to cause the valve to move in a direction from the first position toward the second position.

In some embodiments, the storage chamber is hermetically sealed with respect to ambient atmosphere, is sterile, and includes therein multiple doses of a sterile or aseptic substance. The one-way valve substantially prevents fluid and germ ingress, such as air, therethrough and into the storage chamber.

In some embodiments, the body includes a sliding seal received therein and spaced relative to the one-way valve, wherein the storage chamber is a variable-volume storage chamber defined within the body between the sliding seal and the one-way valve.

In some embodiments, the devices further comprises a base closure sealingly enclosing the body at an opposite side of the body from the one-way valve, and a flexible bladder integrally formed with the base closure and projecting therefrom toward the one-way valve, wherein the storage chamber is a variable-volume storage chamber defined between the flexible bladder and the body. In some such embodiments, the flexible bladder is configured to collapse when the variable-volume storage chamber is filled and expands when substance is dispensed from the variable-volume storage chamber.

In accordance with another aspect, a device for storing multiple doses of a substance to be dispensed into one or more syringes or other delivery devices comprises first means for storing therein multiple doses of the substance, second means for coupling in fluid communication with a syringe or other delivery device and for moving between first and second positions, and for preventing substance from passing through the second means in a closed position and for permitting substance to pass through the second means in an open position, and third means for preventing the second means from opening into the open position in the first position, and for permitting the second means to open into the open position in the second position.

Some embodiments further include fourth means for penetrating with a needle, filling or injection member, and sterile or aseptic filling the substance into the first means. In some such embodiments, the third means is a penetrable and resealable portion or septum.

Some embodiments include means for sterile or aseptic filling the substance into the first means comprising a smooth and non-piercing probe for injecting the fluid through a one-way valve, including a valve comprising a depressible, approximately dome-shaped spring, or other type of elastic spring, with mechanical self-closing properties, after filling and withdrawal of the probe.

Some embodiments further comprise fifth means for connecting thereto the syringe or other delivery device. Some embodiments further comprise sixth means for biasing the second means in the direction from the first position toward the second position. In some embodiments, the first means is a storage chamber (defining either a fixed or variable volume), the second means is a one-way valve, the fifth means is a connector, the sixth means is a spring, the third means is a surface of a body of the device and/or a connector that is engageable with the one-way valve in the first position.

In accordance with another aspect, a method comprises the following steps:
i. storing multiple doses of a substance to be dispensed in a storage chamber and sealing the stored multiple doses with respect to ambient atmosphere;
ii. connecting a syringe or other delivery device in fluid communication with a one-way valve in fluid communication with the storage chamber;
iii. dispensing a dose of substance from the storage chamber through the one-way valve and into the syringe or other delivery device;
iv. substantially preventing ambient fluid from passing through the one-way valve and into the storage chamber during step iii; and
v. repeating steps ii through iv with the same multiple dose device.

In some embodiments, step (iii) includes creating at least a partial vacuum in the syringe or other delivery device and, in turn, creating a pressure differential across the one-way valve that exceeds a valve opening pressure thereof. Some embodiments further include, during or after step ii, moving the one-way valve from (i) a first position where the one-way valve is prevented from opening into an open position wherein substance may pass therethrough, to (ii) a second position where the one-way valve is permitted to open into the open position and substance may pass therethrough. Some embodiments further include engaging the one-way valve with the syringe or other delivery device, and moving the one-way valve in the direction from the first position toward the second position during or after connecting the syringe or other delivery device to the multiple dose device. Some embodiments further comprise maintaining the substance in the storage chamber hermetically sealed with respect to ambient atmosphere throughout steps i through iv.

Some such embodiments further comprise maintaining the substance in the storage chamber sterile or aseptic throughout steps i through iv.

One advantage of the present invention is that the multiple dose device, such as the multiple dose vial, can safely dispense multiple doses of a medicament or other substance without risk of contaminating the substance remaining within the storage chamber after one or more doses are withdrawn, or without the risk of cross-contamination between patients treated with medicament or other substance from the same device. Yet another advantage is that the one-way valve can substantially prevent air and germs from passing through the one-way valve and into the storage chamber, such as during dispensing multiple doses of substance from the storage chamber into a syringe or other delivery device. Yet another advantage is that the device can maintain the substance stored in the storage chamber, such as a medicament, pharmaceutical, vaccine, liquid nutrition product or supplement, sealed with respect to ambient atmosphere and sterile and/or aseptic through dispensing of multiple doses from the device. Yet another advantage is that the device can allow for needleless transfer of doses of substance, such as a medicament, from the device to a syringe, such as through a Luer connection. Yet another advantage is that the device can substantially prevent any ambient or otherwise contaminated air from being injected into the chamber of the device containing the remaining doses of substance to be dispensed.

Other objects and advantages of the present invention, and/or of the currently preferred embodiments thereof, will become more readily apparent in view of the following detailed description of currently preferred embodiments and accompanying drawings.

DETAILED DESCRIPTION OF EMBODIMENTS OF THE INVENTION

Figure 1:
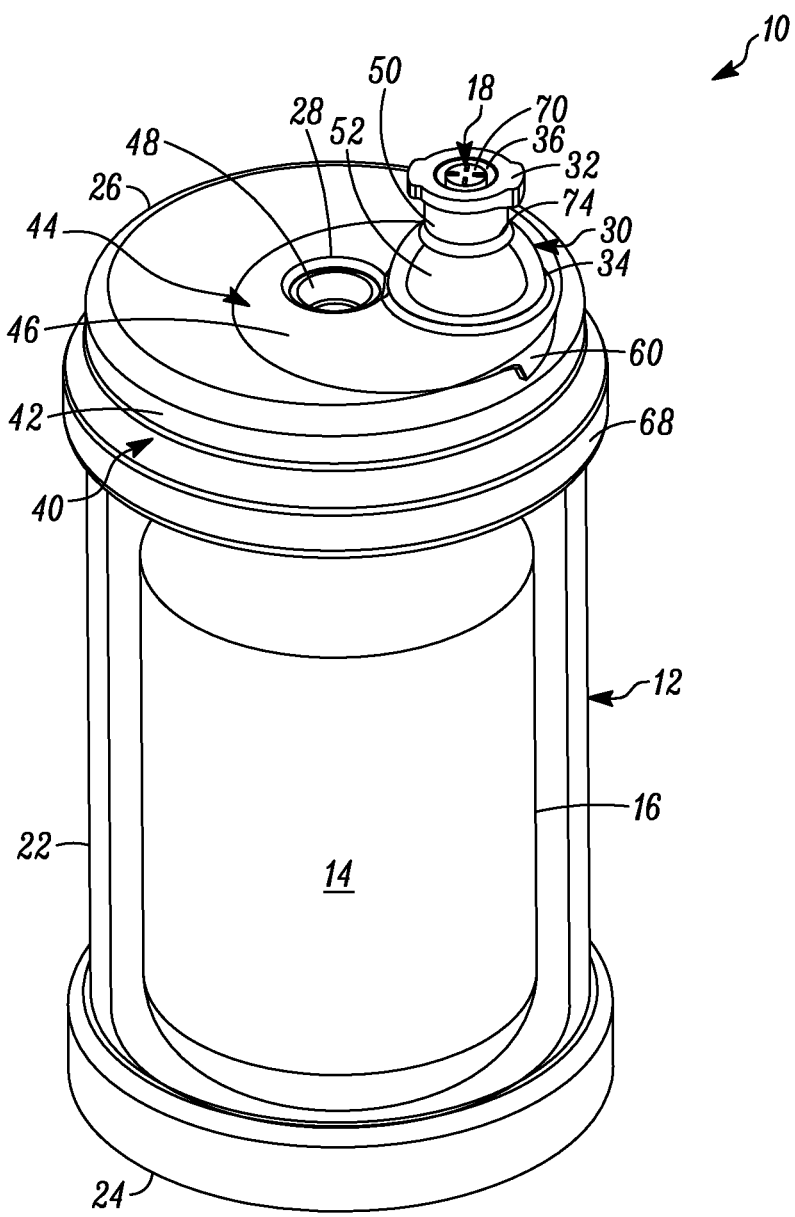
FIG. 1 is a perspective view of a multiple dose vial.

In FIGS. 1-6, a device is indicated generally by the reference numeral 10. In the illustrated embodiment, the device 10 is a multiple dose vial. However, as may be recognized by those of ordinary skill in the pertinent art based on the teachings herein, the invention is applicable to any of numerous other devices or methods that are currently known, or that later become known. The vial 10 comprises a body 12 and a storage chamber 14 within the body for storing multiple doses of the substance therein. In the illustrated embodiment, the storage chamber is a variable-volume storage chamber defined by a flexible and/or elastic pouch 16. A one-way valve 18 is connectable in fluid communication with a syringe 20 (FIGS. 3-6). The one-way valve 18 (i) permits substance from the storage chamber 14 to flow therethrough and into the syringe 20 when connected in fluid communication therewith, and (ii) substantially prevents any fluid flow in a substantially opposite direction therethrough and into the storage chamber 14 to thereby maintain the substance sterile, aseptic and/or contamination free.

The body 12 defines a side wall 22 (here cylindrical but can be another shape), an opening 24 at the base of the side wall, and an upper wall 26 enclosing the body 12 at the opposite end of the base. The upper wall 26 defines a filling port 28 extending through a central region thereof, and a connector 30 including a male Luer connector 32 formed on the outer end thereof, an approximately dome-shaped base 34 extending between the male Luer connector 32 and the upper wall 26, and a valve opening 36 extending through the connector for receiving the one-way valve 18.

Figures 2A, 2B:
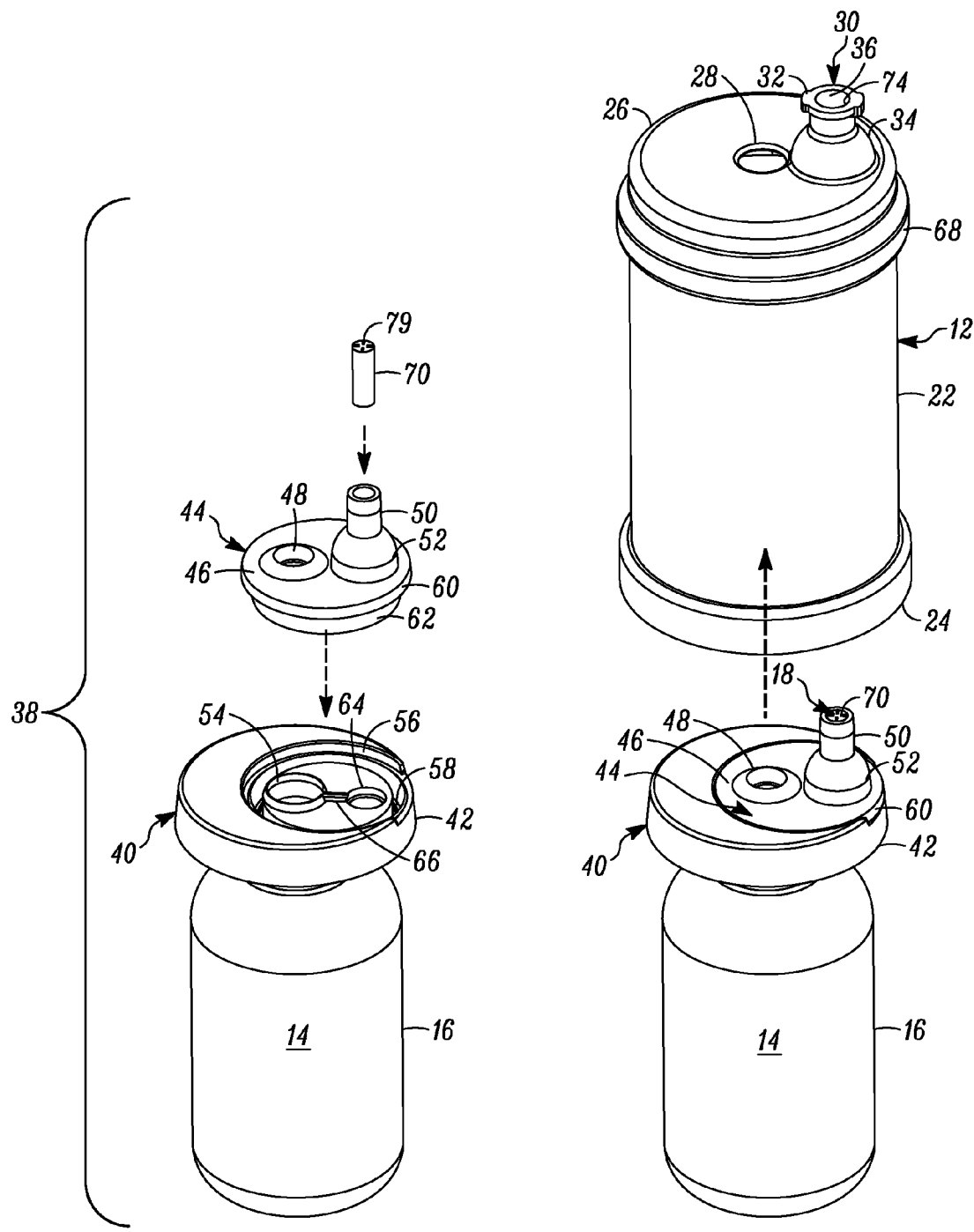
FIG. 2A is an exploded, perspective view of the variable-volume storage chamber, closure and one-way valve of the multiple dose vial of FIG. 1.
FIG. 2B is a perspective view of the assembled variable-volume storage chamber, closure and one-way valve, and illustrating the manner in which the assembly is inserted into the body of the multiple dose vial of FIG. 1.

As shown best in FIGS. 2A and 2B, the vial 10 includes a variable-volume storage chamber, closure and one-way valve preassembly 38 that is received within and fixedly secured to the vial body 12 to form the multiple dose vial. The preassembly 38 comprises a closure 40 including a relatively rigid closure base 42 and a relatively flexible closure overlay 44 mounted on the closure base 42. The flexible closure overlay 44 defines a flexible base and sealing member 46, a penetrable filling portion or septum 48, a valve cover or member 50 of the one-way valve 18, and an approximately dome-shaped spring 52 extending between the valve member 50 and flexible base 46. As can be seen, when the preassembly 38 is assembled to the vial body 12, the valve cover 50 is received within the valve opening 36 of the connector 30, and the dome-shaped spring 52 is received within the dome-shaped base 34 of the connector 30.

As shown in FIGS. 2A and 3-6, the closure base 42 defines a filling inlet 54 that is aligned, e.g., axially, with the filling port 28 of the vial body 12 and opens into the variable-volume storage chamber 14 of the flexible pouch 16. As can be seen, the flexible pouch 16 and filling inlet 54 are integrally formed with the closure base 42. In the illustrated embodiment, the closure base 42, filling inlet 54, and a preform (not shown) for the flexible pouch 16 are injection molded, and the pouch 16 is, in turn, blow molded from the injection molded preform, in accordance with the teachings of any of the following co-pending patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Application No. 61/104,613, filed Oct. 10, 2008; and U.S. patent application Ser. No. 12/901,420, filed Oct. 8, 2010, entitled "Device with Co-Molded Closure, One Way Valve and Variable-Volume Storage Chamber, and Related Method," which claims the benefit of similarly titled U.S. Provisional Application No. 61/250,363, filed Oct. 9, 2009.

As shown in FIG. 2A, the closure base 42 defines a circular-shaped recess 56 that receives therein the flexible base and sealing member 46 of the closure overlay 44. The closure base 42 further defines an annular seal channel 58 spaced radially inwardly relative to the periphery of the circular-shaped recess 56. The flexible closure overlay 44 defines a corresponding peripheral seal 60 and an annular seal 62 spaced radially inwardly relative to the peripheral seal 60 and projecting axially therefrom. The annular seal 62 of the closure overlay 44 is received within the annular seal channel 58 of the closure base 42 to form a fluid-tight seal therebetween, and the peripheral seal 60 of the closure overlay 44 is received within the periphery of the recess 56 of the closure base 42 to form a fluid-tight seal therebetween. The closure base 42 further defines within the circular-shaped recess 56 a valve-receiving recess 64 aligned with the one-way valve 18, and a fluid-flow channel 66 extending between the storage chamber port 54 and the valve-receiving recess 64. As described further below, when the syringe 20 is fully connected to the connector 30, the one-way valve 18 is moveable from a first normally-closed position (FIG. 5) to a second position (FIG. 6) which, in turn, allows fluid to be withdrawn by the syringe 20 from the variable-volume storage chamber 14, through the storage chamber port 54, fluid flow channel 66, and one-way valve 18 and, in turn, into the syringe 20. As shown best in FIGS. 4-6, the vial body 12 defines a snap-fit protuberance 68 that is axially spaced adjacent to the upper wall 26 and extends annularly about the vial body. As can be seen, the side of the protuberance 68 opposite the upper wall 26 is tapered inwardly to allow the closure 40 to slide past the protuberance and into the assembled position as shown. The protuberance 68 engages the underside of the closure base 42 to form a compression seal between peripheral seal 60 and annular seal 62 of the flexible overlay 44 and the closure base 42, hermetically seal the variable-volume storage chamber 14 with respect to ambient atmosphere, and fixedly secure the closure base 42 and thus the preassembly 38 within the vial body 12. As should be understood by those of ordinary skill in the pertinent art, the components of the vial may take any of numerous different shapes and/or configurations capable of performing the function(s) of each such component as described herein.

The septum 48 is penetrable by a needle, filling or injection member (not shown) for sterile or aseptically filling the storage chamber 14 with multiple doses of the substance to be dispensed. The septum 48, in some embodiments, is formed of a material that is sufficiently elastic to close itself after withdrawal of the needle, filling or injection member therefrom to thereby ensure that the head loss left by a residual penetration hole after the injection member is withdrawn prevents fluid ingress therethrough. Although such a septum 48 is self-closing, the septum may be resealed by a liquid sealant such as silicone or a silicone-based sealant, and/or the application of radiation or energy thereto to hermetically seal the substance within the storage chamber 14 from the ambient atmosphere and thereby maintain the sterility of the substance.

For example, the septum 48 may be penetrable for sterile filling the variable-volume storage chamber 14 and resealable, such as by the application of laser, other radiation, or thermal energy, to hermetically seal the filled substance within the storage chamber 14 in accordance with the teachings of any of the following patents and patent applications, each of which is hereby expressly incorporated by reference in its entirety as part of the present disclosure: U.S. patent application Ser. No. 12/254,789, filed Oct. 20, 2008, entitled "Container Having a Closure and Removable Resealable Stopper for Sealing a Substance Therein and Related Method," which, in turn, claims the benefit of U.S. Patent Application No. 60/981,107, filed Oct. 18, 2007, entitled "Container Having a Closure and Removable Resealable Stopper for Sealing a Substance Therein;" U.S. patent application Ser. No. 12/245,678, filed Oct. 3, 2008, entitled "Apparatus For Formulating and Aseptically Filling Liquid Products," and U.S. patent application Ser. No. 12/245,681, filed Oct. 3, 2008, entitled "Method For Formulating and Aseptically Filling Liquid Products," which, in turn, claim the benefit of U.S. Patent Application No. 60/997,675, filed Oct. 4, 2007, entitled "Apparatus and Method for Formulating and Aseptically Filling Liquid Products;" U.S. patent application Ser. No. 12/875,440, filed Sep. 3, 2010, entitled "Device with Needle Penetrable and Laser Resealable Portion and Related Method," now U.S. Pat. No. 7,980,276, which is a divisional of U.S. patent application Ser. No. 12/371,386, filed Feb. 13, 2009, entitled "Device with Needle Penetrable and Laser Resealable Portion," now U.S. Pat. No. 7,810,529, which is a continuation of U.S. patent application Ser. No. 11/949,087, filed Dec. 3, 2007, entitled "Device with Needle Penetrable and Laser Resealable Portion and Related Method," now U.S. Pat. No. 7,490,639, which is a continuation of similarly titled U.S. patent application Ser. No. 11/879,485, filed Jul. 16, 2007, now U.S. Pat. No. 7,445,033, which is a continuation of similarly titled U.S. patent application Ser. No. 11/408,704, filed Apr. 21, 2006, now U.S. Pat. No. 7,243,689, which is a continuation of U.S. patent application Ser. No. 10/766,172, filed Jan. 28, 2004, entitled "Medicament Vial Having a Heat-Sealable Cap, and Apparatus and Method for Filling the Vial," now U.S. Pat. No. 7,032,631, which is a continuation-in-part of similarly titled U.S. patent application Ser. No. 10/694,364, filed Oct. 27, 2003, now U.S. Pat. No. 6,805,170 which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed Feb. 11, 2000, and similarly titled U.S. Provisional Patent Application No. 60/443,526, filed Jan. 28, 2003, and similarly titled U.S. Provisional Patent Application No. 60/484,204, filed Jun. 30, 2003; U.S. patent application Ser. No. 13/193,662, filed Jul. 29, 2011, entitled "Sealed Contained and Method of Filling and Resealing Same," which is a continuation of U.S. patent application Ser. No. 12/791,629, filed Jun. 1, 2010, entitled "Sealed Containers and Methods of Making and Filling Same," now U.S. Pat. No. 7,992,597, which is a divisional of U.S. patent application Ser. No. 11/515,162, filed Sep. 1, 2006, entitled "Sealed Containers and Methods of Making and Filling Same," now U.S. Pat. No. 7,726,352, which is a continuation of U.S. patent application Ser. No. 10/655,455, filed Sep. 3, 2003, entitled "Sealed Containers and Methods of Making and Filling Same," now U.S. Pat. No. 7,100,646, which is a continuation-in-part of U.S. patent application Ser. No. 10/393,966, filed Mar. 21, 2003, entitled "Medicament Vial Having A Heat-Sealable Cap, and Apparatus and Method For Filling The Vial," now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed on Feb. 11, 2000, and U.S. Provisional Patent Application No. 60/408,068, filed Sep. 3, 2002, entitled "Sealed Containers and Methods Of Making and Filling Same;" U.S. patent application Ser. No. 12/627,655, filed Nov. 30, 2009, entitled "Adjustable Needle Filling and Laser Sealing Apparatus and Method," now U.S. Pat. No. 8,096,333, which is a continuation of similarly titled U.S. patent application Ser. No. 10/983,178, filed Nov. 5, 2004, now U.S. Pat. No. 7,628,184, which, in turn, claims the benefit of U.S. Provisional Patent Application No. 60/518,267, filed Nov. 7, 2003, entitled "Needle Filling and Laser Sealing Station," and similarly titled U.S. Provisional Patent Application No. 60/518,685, filed Nov. 10, 2003; U.S. patent application Ser. No. 11/901,467, filed Sep. 17, 2007 entitled "Apparatus and Method for Needle Filling and Laser Resealing," which is a continuation of similarly titled U.S. patent application Ser. No. 11/510,961 filed Aug. 28, 2006, now U.S. Pat. No. 7,270,158, which is a continuation of similarly titled U.S. patent application Ser. No. 11/070,440, filed Mar. 2, 2005; now U.S. Pat. No. 7,096,896, which, in turn, claims the benefit of U.S. Provisional Patent Application No. 60/550,805, filed Mar. 5, 2004, entitled "Apparatus for Needle Filling and Laser Resealing;" U.S. patent application Ser. No. 12/768,885, filed Apr. 28, 2010, entitled "Apparatus for Molding and Assembling Containers with Stoppers and Filling Same," now U.S. Pat. No. 7,975,453, which is a continuation of similarly titled U.S. patent application Ser. No. 11/074,513, filed Mar. 7, 2005, now U.S. Pat. No. 7,707,807, which claims the benefit of U.S. Provisional Patent Application No. 60/551,565, filed Mar. 8, 2004, entitled "Apparatus and Method For Molding and Assembling Containers With Stoppers and Filling Same;" U.S. patent application Ser. No. 13/396,053, filed Feb. 14, 2012, entitled "Method for Molding and Assembling Containers with Stopper and Filling Same," which is a continuation of similarly titled U.S. patent application Ser. No. 12/715,821, filed Mar. 2, 2010, now U.S. Pat. No. 8,112,972, which is a continuation of similarly titled U.S. patent application Ser. No. 11/074,454, filed Mar. 7, 2005, now U.S. Pat. No. 7,669,390; U.S. patent application Ser. No. 11/339,966, filed Jan. 25, 2006, entitled "Container Closure With Overlying Needle Penetrable and Thermally Resealable Portion and Underlying Portion Compatible With Fat Containing Liquid Product, and Related Method," now U.S. Pat. No. 7,954,521, which, in turn, claims the benefit of U.S. Provisional Patent Application No. 60/647,049, filed Jan. 25, 2005, entitled "Container with Needle Penetrable and Thermally Resealable Stopper, Snap-Ring, and Cap for Securing Stopper;" U.S. patent application Ser. No. 12/861,354, filed Aug. 23, 2010, entitled "Ready To Drink Container With Nipple and Needle Penetrable and Laser Resealable Portion, and Related Method;" which is a divisional of similarly titled U.S. patent application Ser. No. 11/786,206, filed Apr. 10, 2007, now U.S. Pat. No. 7,780,023, which, into turn, claims the benefit of similarly titled U.S. Provisional Patent Application No. 60/790,684, filed Apr. 10, 2006; U.S. patent application Ser. No. 11/295,251, filed Dec. 5, 2005, entitled "One-Way Valve, Apparatus and Method of Using the Valve," now U.S. Pat. No. 7,322,491, which, in turn, claims the benefit of similarly titled U.S. Provisional Patent Application No. 60/644,130, filed Jan. 14, 2005, and similarly titled U.S. Provisional Patent Application No. 60/633,332, filed Dec. 4, 2004; U.S. patent application Ser. No. 12/789,565, filed May 28, 2010, entitled "Resealable Containers and Methods of Making, Filling and Resealing the Same," which is a continuation of U.S. patent application Ser. No. 11/933,272, filed Oct. 31, 2007, entitled "Resealable Containers and Assemblies for Filling and Resealing Same," now U.S. Pat. No. 7,726,357, which is a continuation of U.S. patent application Ser. No. 11/515,162, filed Sep. 1, 2006, entitled "Sealed Containers and Methods of Making and Filling Same," now U.S. Pat. No. 7,726,352; U.S. patent application Ser. No. 13/045,655, filed Mar. 11, 2011, entitled "Sterile Filling Machine Having Filling Station and E-Beam Chamber," which is a continuation of U.S. patent application Ser. No. 12/496,985, filed Jul. 2, 2009, entitled "Sterile Filling Machine Having Needle Filling Station and Conveyor," now U.S. Pat. No. 7,905,257, which is a continuation of U.S. patent application Ser. No. 11/527,775, filed Sep. 25, 2006, entitled "Sterile Filling Machine Having Needle Filling Station within E-Beam Chamber," now U.S. Pat. No. 7,556,066, which is a continuation of similarly titled U.S. patent application Ser. No. 11/103,803, filed Apr.

11, 2005, now U.S. Pat. No. 7,111,649, which is a continuation of similarly titled U.S. patent application Ser. No. 10/600,525, filed Jun. 19, 2003, now U.S. Pat. No. 6,929,040, which, in turn, claims the benefit of similarly-titled U.S. Provisional Patent Application No. 60/390,212, filed Jun. 19, 2002; U.S. patent application Ser. No. 13/326,177, filed Dec. 14, 2011, entitled "Device with Penetrable and Resealable Portion and Related Method," which is a continuation of similarly titled U.S. patent application Ser. No. 13/170,613, filed Jun. 28, 2011, now U.S. Pat. No. 8,347,923, which is a continuation of U.S. patent application Ser. No. 12/401,567, filed Mar. 10, 2009, entitled "Device with Needle Penetrable and Laser Resealable Portion and Related Method," now U.S. Pat. No. 7,967,034, which is a continuation of similarly titled U.S. patent application Ser. No. 11/933,300, filed Oct. 31, 2007, now U.S. Pat. No. 7,500,498; U.S. patent application Ser. No. 13/329,483, filed Apr. 30, 2011, entitled "Ready to Feed Container," which is a continuation of International Application No. PCT/US2011/034703, filed Apr. 30, 2011, entitled "Ready to Feed Container and Method," which, in turn, claims the benefit of U.S. Provisional Patent Application No. 61/330,263 filed Apr. 30, 2010; and U.S. Provisional Patent Application No. 61/476,523, filed Apr. 18, 2011, entitled "Filling Needle and Method."

Alternatively, the septum 48 may be penetrable for sterile filling the variable-volume storage chamber 14 and resealable with a liquid sealant, such as a silicone sealant, to hermetically seal the filled substance within the storage chamber 14, in accordance with the teachings of any of the following patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Patent Application No. 61/104,613, filed Oct. 10, 2008; U.S. patent application Ser. No. 12/901,420, filed Oct. 8, 2010, entitled "Device with Co-Molded One-Way Valve and Variable Volume Storage Chamber and Related Method," which claims the benefit of similarly titled U.S. Provisional Patent Application No. 61/250,363, filed Oct. 9, 2009; and U.S. Provisional Patent Application No. 61/476,523, filed Apr. 18, 2011, entitled "Filling Needle and Method."

Prior to filling the variable-volume storage chamber 14, the sealed empty chamber may be sterilized by injecting a fluid sterilant therein, such as nitric oxide, with a needle, filling, or injection member through the penetrable and resealable portion 48, and the needle employed for injecting the fluid sterilant and/or the substance to be sterile filled into the variable-volume storage chamber 14 may be a self-opening and closing needle, in accordance with the teachings of any of the following co-pending patent applications, each of which is hereby expressly incorporated by reference in its entirety as part of the present disclosure: U.S. patent application Ser. No. 13/450,306, filed Apr. 18, 2012, entitled "Needle with Closure and Method," which claims the benefit of U.S. Provisional Patent Application No. 61/476,523, filed Apr. 18, 2011, entitled "Filling Needle and Method;" and U.S. patent application Ser. No. 13/529,951, filed Jun. 21, 2012, entitled "Fluid Sterilant Injection Sterilization Device and Method," which claims the benefit of U.S. Provisional Patent Application No. 61/499,626, filed Jun. 21, 2011, entitled "Nitric Oxide Injection Sterilization Device and Method." As may be recognized by those of ordinary skill in the pertinent art based on the teachings herein, the penetrable and resealable portion or septum may be penetrated and resealed, and the variable-volume storage chamber may be sterilized and sterile filled, by any of numerous different devices and methods that are currently known, or that later become known.

Figure 4:
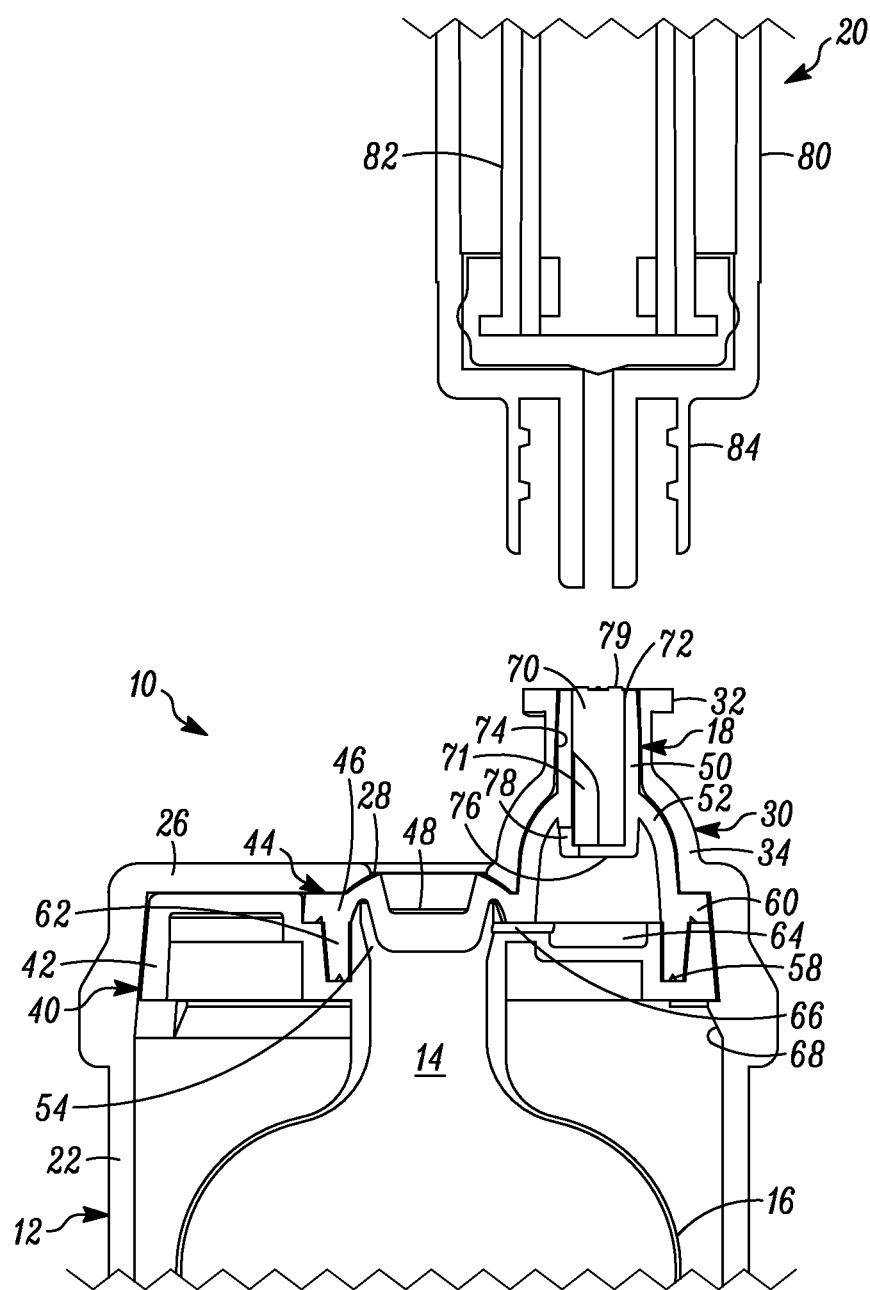
FIG. 4 is an enlarged, partial cross-sectional view of the upper portion of the multiple dose vial of FIG. 1 illustrating the one-way valve in the first or normally-closed position, and an enlarged cross-sectional view of the tip of a syringe prior to connection to the vial.
Figure 5:
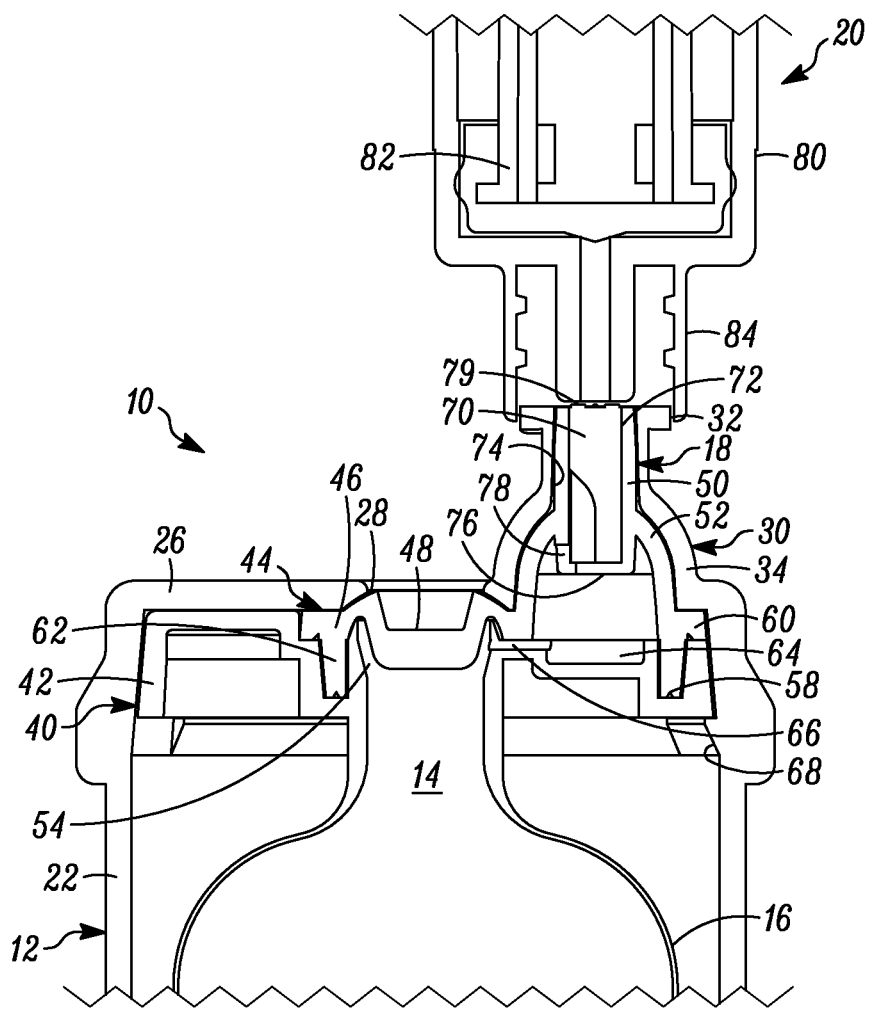
FIG. 5 is the same view as FIG. 4 but illustrating the female Luer connector of the syringe placed into engagement with the male Luer connector of the multiple dose vial.
Figure 6:
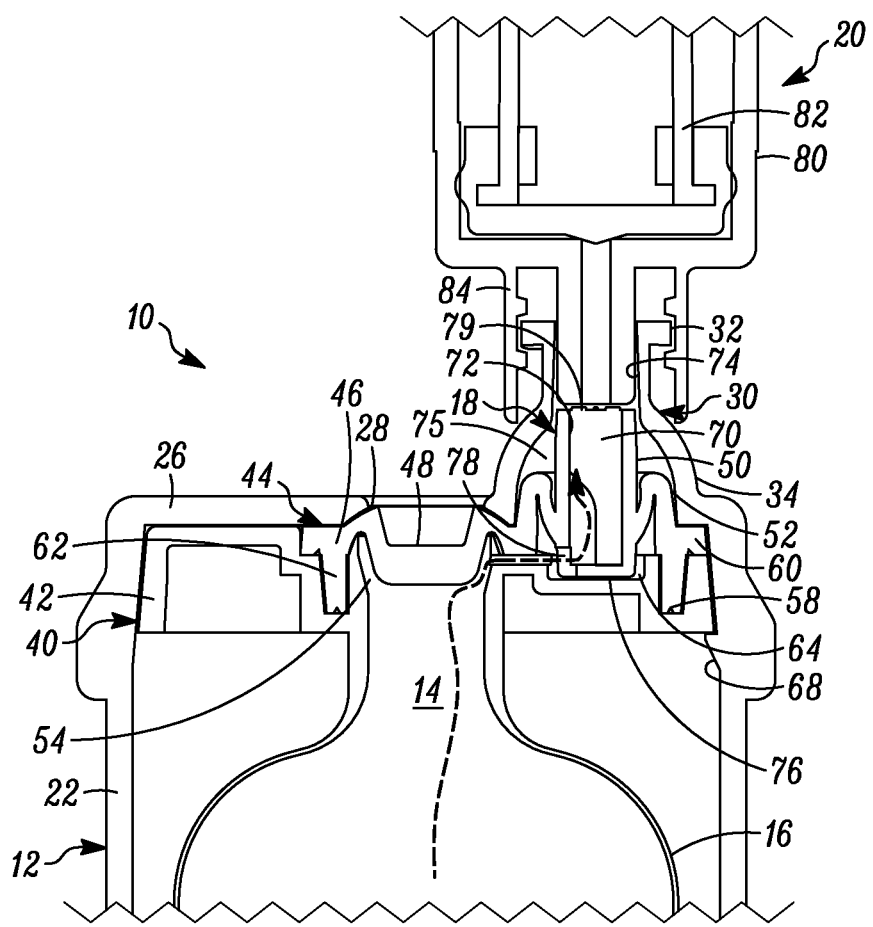
FIG. 6 is the same view as FIGS. 4 and 5, but illustrating the female Luer connector of the syringe fully engaged with the male Luer connector of the multiple dose vial, and the one-way valve in the second position allowing one or more doses of the stored substance to be withdrawn from the storage chamber, through the one-way valve, and into the body of the syringe.

As shown best in FIGS. 4-6, the one-way valve 18 includes a relatively rigid valve seat 70 that is received within the flexible valve member or cover 50 and defines a normally closed, valve seam 72 therebetween. In the illustrated embodiment the valve seam 72 is axially-elongated and annular, but can have other shapes and configurations. The valve member 50 engages, and in some embodiments forms an interference fit with, the valve seat 70 to thereby form a fluid-tight seal in the normally closed position and, in turn, maintain the substance within the storage chamber 14 in a sterile and hermetically sealed condition. The valve 18 defines a valve opening pressure and remains in the normally closed position unless a pressure differential across the valve exceeds the valve opening pressure. When a pressure differential across the valve does exceed the valve opening pressure, the valve member 50 expands, e.g., radially, relative to or otherwise moves away from the valve seat 70 and opens the valve seam 72 therebetween.

The valve opening pressure is defined, in part, as a function of the length of the engagement of the valve member 50 with the valve seat 70, i.e., the axial extent of the valve seam 72. The greater the length thereof, the greater the valve opening pressure. As shown, the valve seat 70 defines at least one elongated groove 71 therein. Thus, the valve member 50 need not be displaced at the groove(s) 71 for the fluid to flow. Accordingly, the length, and number, of the groove(s) 71 effectively reduces the length of the valve seam 72 and thus effectively reduces the valve opening pressure of the valve 18. The length and number of the groove(s) 71 are configured, in consideration of the properties of the valve member 50, e.g., its elasticity, thickness, shape, etc., such that a delivery device engaging the valve 18 and utilized in a normal manner, e.g., withdrawing a plunger from a barrel of a syringe engaging the valve, is capable of creating a pressure differential across the valve that exceeds the valve opening pressure, and this opens the valve seam 72. Conversely, these features are configured to maintain a minimum valve opening pressure to prevent unintentional opening, as should be understood by one of ordinary skill in the pertinent art.

Figure 7:
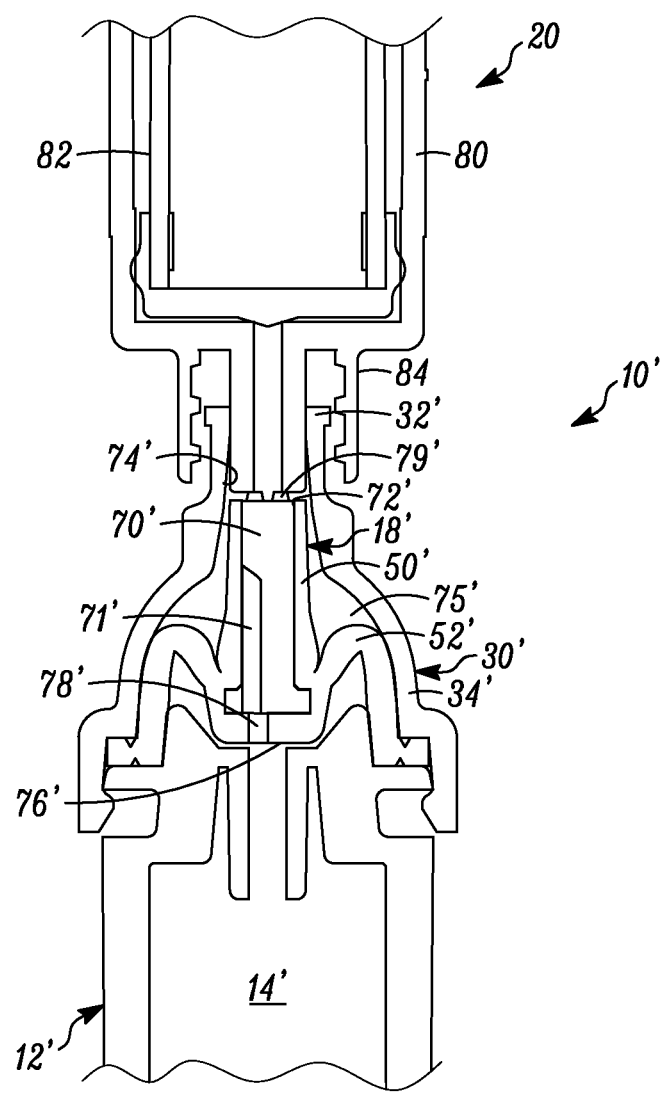
FIG. 7 is an enlarged, partial cross-sectional view of the upper portion of a multiple dose vial, illustrating the one-way valve in the second position where the connector defines a tapered interior surface.
Figure 10:
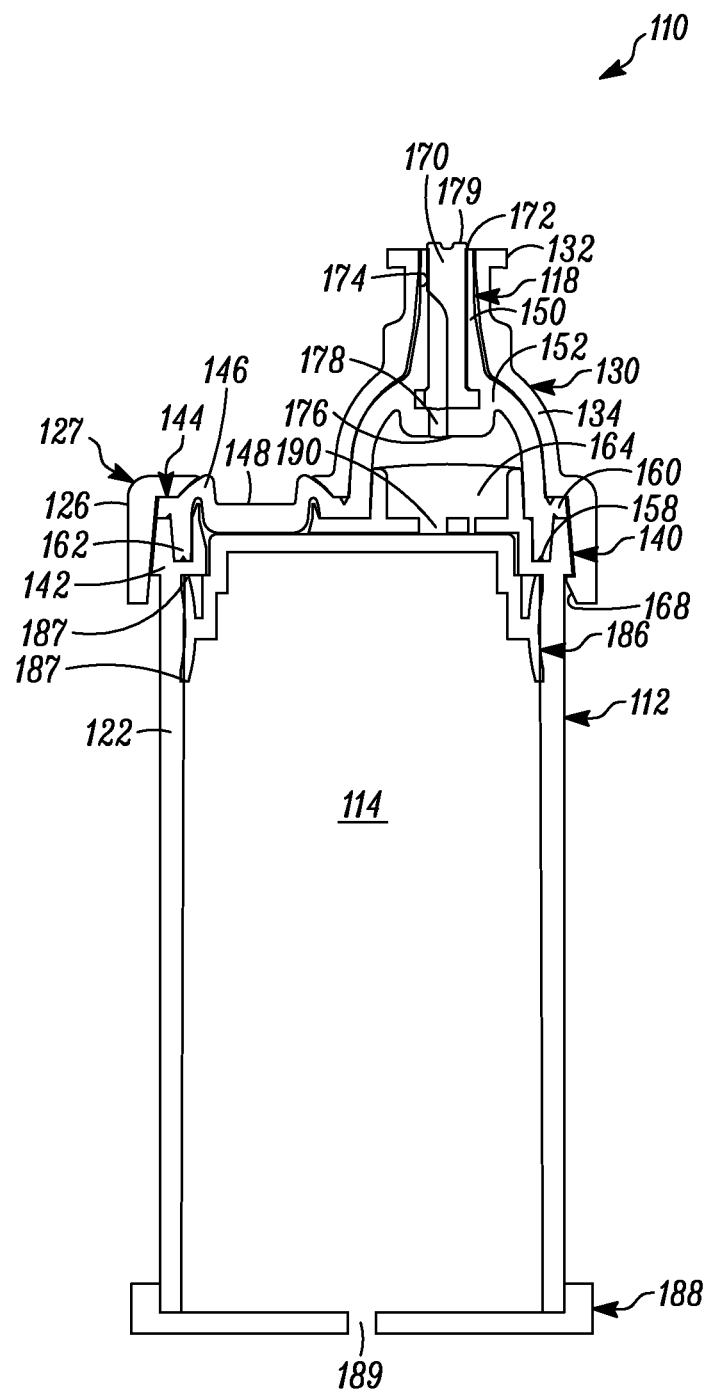
FIG. 10 is a cross-sectional view of the multiple dose vial of FIG. 8 with the sliding seal in an empty storage chamber.

In some embodiments, such as seen in FIGS. 7 and 10, the valve member 50', 150 may also define a substantially tapered cross-sectional shape moving in the direction from an inlet towards an outlet of the valve. This configuration requires progressively less energy to open the valve when moving from the interior, or inlet, toward the exterior, or outlet, of the valve. Alternatively, or in combination with the tapered valve member 50', 150, the valve seat 70', 170 may define an outer diameter that progressively or otherwise increases in the direction from the inlet towards the outlet of the valve, to provide the same or similar effect. As a result, once the pressure is sufficient to open the valve at an inlet thereof, the pressure is sufficient to cause the downstream segments or portions of the valve member 50', 150 to progressively open and then close after passage of substance through the respective portion of the valve seam 72', 172 when moving in the direction from the inlet towards the outlet of the valve to dispense the dosage of substance. Also, in some embodiments, at any time when dispensing a dosage of substance, at least one of the plurality of segments of the valve member 50 engages the valve seat 70 to maintain a fluid-tight seal across the valve 18, and thereby prevent ingress of fluid, germs, bacteria or other unwanted substances therethrough and into the variable-volume storage chamber 14.

As indicated above, the valve 18 includes a substantially dome-shaped spring 52 formed of a resilient and/or elastomeric material. The spring 52 permits the valve member 18 to move between an extended first position (FIG. 5), wherein the valve member 50 is fully received within the valve opening 36 of the connector, and a depressed second position (FIG. 6) wherein the valve member 50 is depressed or otherwise moved distally within the valve opening 36 and out of engagement with the interior surface 74 of the connector 30. As can be seen, the dome-shaped spring 52 normally biases the valve 18 in the direction from the second position toward the first position. The spring 52 also substantially prevents pressure created by inadvertently ejected air or other material from a syringe or other delivery device 20 connected to the valve 18 from moving the valve from the first position toward the second position.

When in the first position (FIG. 5), the interior surface 74 forming the valve opening 36 engages the valve member 50 or otherwise substantially prevents expansion or opening of the valve member 50 relative to the valve seat 70, and thus prevents the valve 18 from opening. The valve seam 72 is closed, thereby preventing the passage of the substance therethrough. When in the second position (FIG. 6), on the other hand, the valve member 50 is disengaged from the interior surface 74 with sufficient space around it so that the valve 18 is free to open (and open the valve seam 72) when a pressure differential across the valve 18 exceeds the valve opening pressure to, in turn, permit expansion of the valve member 50 relative to the valve seat 70 and thereby allow the flow of substance from the variable-volume storage chamber therethrough.

The flexible valve member 50 defines a base portion 76 that engages a distal base of the valve seat 70 to support the valve seat, e.g., axially, within the valve 18. The base portion 76 defines one or more valve inlet apertures 78 therethrough, in fluid communication with the normally closed valve seam 72, to permit fluid flow from the variable-volume storage chamber 14 and through the valve seam 72, when the valve 18 is in the second position and the pressure differential across the valve exceeds the valve opening pressure. The outlet end of the valve seat 70 defines a plurality of angularly spaced protuberances 79 thereon that engage a syringe connector 84 of the syringe 20 and permit the flow of fluid therebetween (between the protuberances 79) in order to allow fluid flow through the valve 18 and into the syringe 20.

Figure 3:
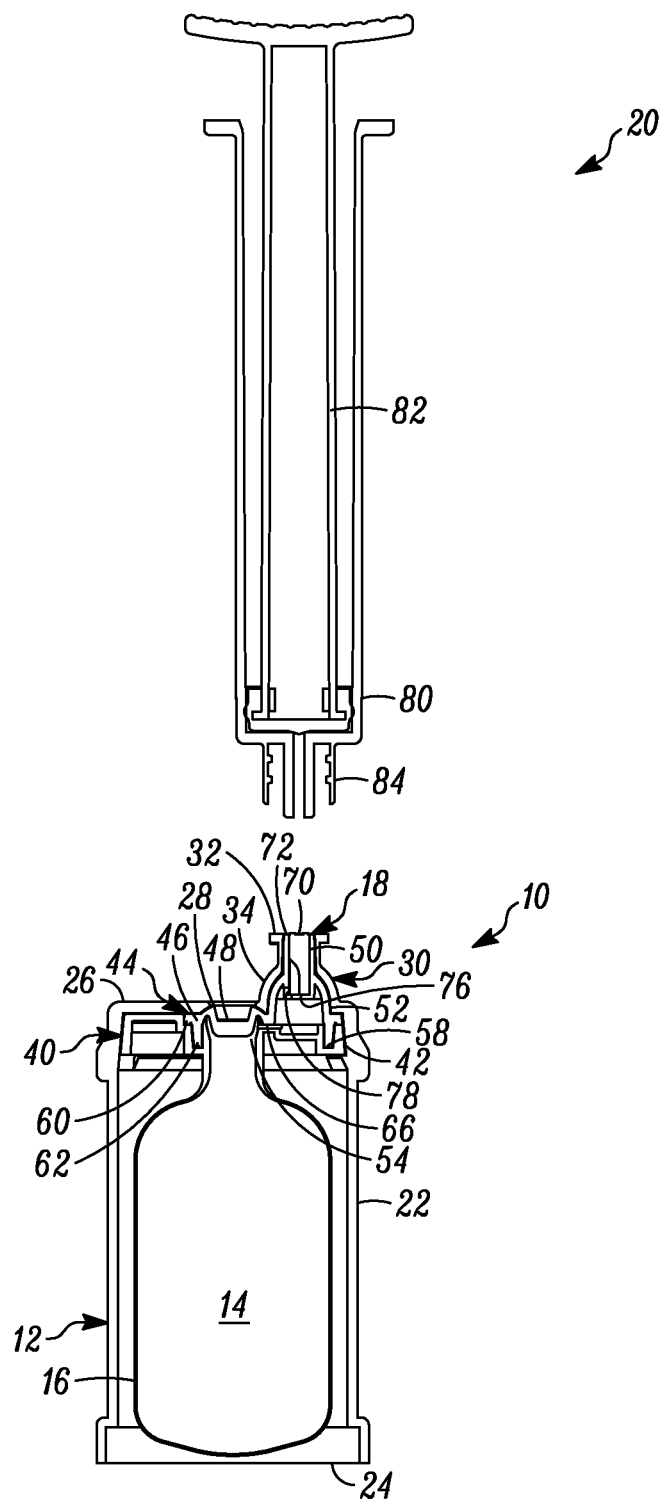
FIG. 3 is a cross-sectional view of the multiple dose vial of FIG. 1 and a syringe connectable to the one-way valve for withdrawing one or more doses of the stored substance from the variable-volume storage chamber of the vial.

In order to dispense the substance from the vial 10, the syringe or other delivery device 20 is connected to the connector 30. As shown in FIG. 3, the syringe 20 includes a barrel 80, a manually-engageable plunger 82 received within the barrel, and the connector 84 mounted at one end of the barrel and in fluid communication with the interior of the barrel. In the illustrated embodiment, the vial connector 30 is a male Luer connector, and the syringe connector 84 is a female Luer connector. However, as may be recognized by those of ordinary skill in the pertinent art based on the teachings herein, any of numerous different connectors for either the syringe or other delivery device, or the multiple dose vial or other device, that are currently known, or that later become known, may be used.

When connected to the vial 10, as shown, for example, in FIGS. 5 and 6, the connector 84 of the syringe 20 engages the valve seat 70 and displaces the valve 18 from the first position toward the second position. When in the second position, the connector 30 and the valve 18 define a cavity 75 therebetween. Thus, if the plunger 82 of the syringe 20 is mistakenly depressed further into barrel of the syringe 20, thereby ejecting air (or other substances) therefrom, the valve 18 remains closed and the ejected material does not flow therethrough, but rather enters into the cavity 75 surrounding the valve 18. The pressure of the air in the cavity 75 functions to further compress the flexible valve member 50 onto the valve seat 70, i.e., helping to keep the valve 18 closed, thereby further ensuring no entry of material through the valve 18 and into the storage chamber 14. In some embodiments, such as shown in FIG. 7, the interior surface 74' of the connector 30' defines a substantially tapered cross-sectional shape moving in the direction from the dome shaped base 34' toward the Luer connector 32', thereby requiring relatively less movement (compared to embodiments where the interior surface 74' is not tapered) of the valve 18' in the direction from the first position toward the section position in order to disengage the interior surface 74' from the valve member 50'. Thus, the cavity 75' is larger in or to accommodate a greater volume of inadvertently ejected air, and further compress the valve 18'. The taper is also sufficient so that the valve member 50' can move away from the valve seat 70' and open the valve 18'.

Conversely, when in the second position and upon withdrawal of the plunger 82 of the syringe 20, a vacuum or partial vacuum is created within the barrel of the syringe 20 which, in turn, creates a pressure differential across the valve 18. When the pressure differential across the valve 18 exceeds the valve opening pressure, the valve seam 72 opens, and the substance within the variable-volume storage chamber 14 flows through the valve inlet aperture(s) 78 and, in turn, through the valve seam 72 and into the barrel of the syringe. Because the valve 18 is in the second position, the valve member 50 is permitted to move relative to the valve seat 70, e.g., radially, to allow the flow of the substance from the variable-volume storage chamber therethrough and into the syringe. However, because of the nature of the valve member 50, any ambient air or other fluid that could contaminate the interior of the valve or storage chamber is substantially prevented from flowing through the valve in the opposite direction, as discussed above. As a result, the interior of the valve and storage chamber can be maintained sterile, aseptic, and/or contamination free, as desired, throughout dispensing of dosages from the storage chamber. When withdrawal of the syringe plunger 82 is terminated, the pressure differential, if any, across the valve 18 decreases to than the valve opening pressure, the valve seam 72 closes (the valve member 50 moves back into engagement with the valve seat 70) and the flow of substance from the variable-volume storage chamber 14 through the valve 18 is terminated.

Upon disconnection, e.g., unscrewing, of the syringe connector 84 from the vial connector 30, the dome-shaped spring 52 drives the valve from the second position toward the first position where the interior surface 74 of the connector engages the valve member 50 and further prevents the possibility of the valve seam 72 opening and any fluid flow through the valve. In embodiments as in FIG. 7 where the interior surface 74' is tapered, the taper assists in guiding the valve 18 into the first position. Thus, the valve 18 permits substance from the variable-volume storage chamber 14 to flow through the one-way valve and into the delivery device connected in fluid communication therewith, but prevents the ingress of fluid in a substantially opposite direction into the variable-volume storage chamber. Consequently, the substance within the variable-volume storage chamber 14 is never exposed to the ambient atmosphere. When another dose of substance is needed from the vial, the same steps may be repeated.

Figure 8:
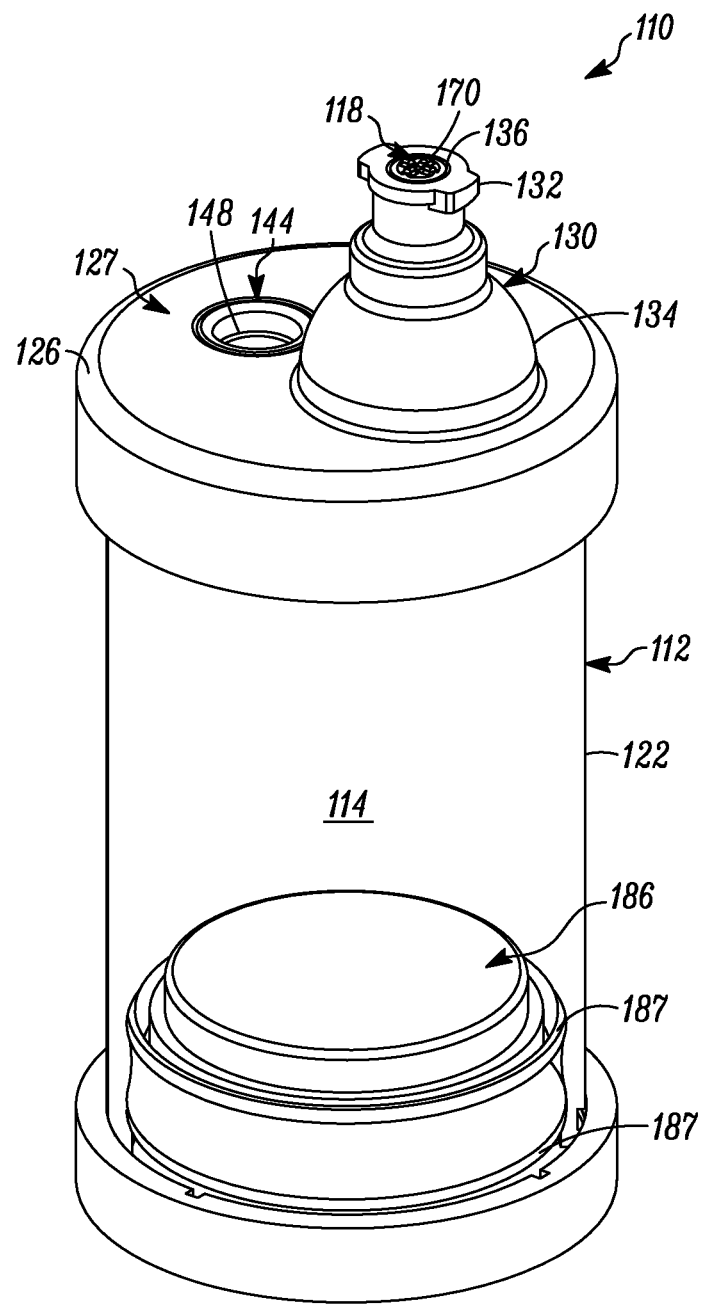
FIG. 8 is a perspective view of another embodiment of a multiple dose vial including a sliding seal received within the vial body, spaced relative to the one-way valve, and defining the variable-volume storage chamber between the sliding seal and the one-way valve.
Figure 9:
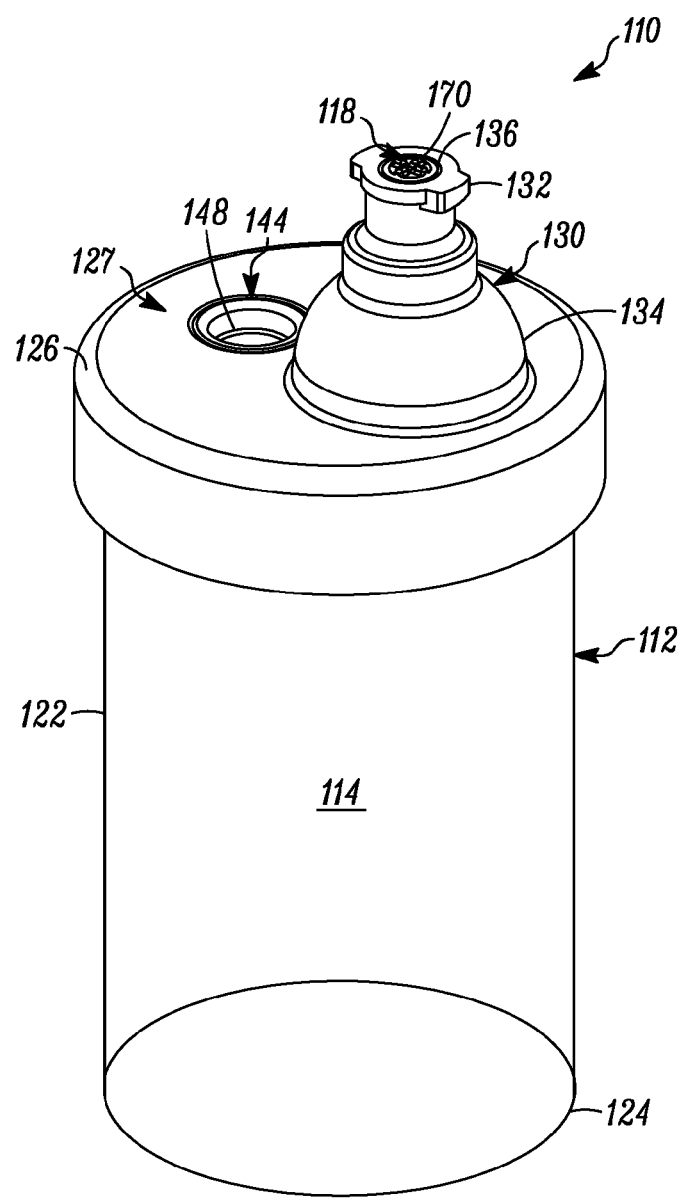
FIG. 9 is an exploded, perspective view of the vial body and the sliding seal of the multiple dose vial of FIG. 8.
Figure 9:
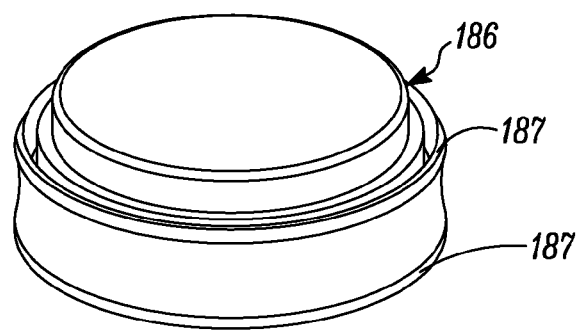

In FIGS. 8-10, another device is indicated generally by the reference numeral 110. The device 110 is substantially similar to the devices 10, 10' described above in connection with FIGS. 1-7, and therefore like reference numerals preceded by the numeral "1" are used to indicate like elements. A primary difference of the device 110 in comparison to the device 10 is that a sliding seal or stopper 186 is received within the vial body 112 and is spaced relative to the one-way valve 118, wherein the variable-volume storage chamber 114 is defined between the sliding seal 186 and the one-way valve 118, as hereinafter described.

The sliding seal 186 includes at least one, and in the embodiment shown, best seen in FIG. 9, two axially spaced outer annular sealing members or portions 187 that sealingly engage the interior cylindrical wall of the vial body 112 to form a fluid-tight seal therebetween, but permit the sliding stopper to slide within the vial body. The sealing members or portions 187 may be formed integral with the sliding seal 186, such as by forming thereon annular protuberances, as shown, or may be formed by sealing members, such as o-rings or other sealing members, that are received within corresponding grooves or recesses formed in the sliding seal. A removable base closure 188 encloses the opening 124 at the base of the vial body 112, and includes one or more vent apertures 189 to prevent the formation of a vacuum between the sliding seal 186 and the base closure 188, and otherwise to allow the sliding seal 186 to travel through the vial body 112 upon dispensing of the substance from the vial 110, as described further below.

The sliding seal 186 and the manner in which it cooperates with the vial body 112 to define the variable-volume storage chamber 114 may be the same as or substantially similar to that disclosed in any of the following patents and patent applications, each of which is hereby expressly incorporated by reference in its entirety as part of the present disclosure: U.S. patent application Ser. No. 13/219,597, filed Aug. 26, 2011, entitled "Laterally-Actuated Dispenser with One-Way Valve For Storing and Dispensing Substances," which is a continuation of U.S. patent application Ser. No. 12/710,516, filed Feb. 23, 2010, entitled "Laterally-Actuated Dispenser with One-Way Valve for Storing and Dispensing Metered Amounts of Substances," now U.S. Pat. No. 8,007,193, which is a continuation of similarly titled U.S. patent application Ser. No. 11/237,599, filed Sep. 27, 2005, now U.S. Pat. No. 7,665,923, which, in turn, claims the benefit of similarly titled U.S. Provisional Patent Application No. 60/613,583, filed Sep. 27, 2004, and similarly titled U.S. Provisional Application No. 60/699,607 filed Jul. 15, 2005; and U.S. patent application Ser. No. 13/743,661, filed Jan. 17, 2013, entitled "Multiple Dose Syringe and Method," which, in turn, claims the benefit of similarly titled U.S. Provisional Patent Application No. 61/587,500, filed Jan. 17, 2012.

In the illustrated embodiment, the closure 140, including the closure base 142, is integrally formed with the upper side of the vial body 112, and the flexible closure overlay 144 is mounted thereon in the same manner as in the embodiments described above in connection with FIGS. 1-7. A vial cap 127, defining the upper wall 126 and connector 130, mounts atop the closure overlay 144 to sealingly enclose the body 112 at the upper side of the vial 110. The vial cap 127 further defines the snap-fit protuberance 168 that is axially spaced adjacent to the upper wall 126 and extends annularly about the cap 127. The side of the protuberance 168 opposite the upper wall 126 is tapered inwardly to allow the closure base 142 of the vial body 112 to slide over the protuberance and snap into the assembled position as shown. The protuberance 168 engages the underside of the closure base 142 to form a compression seal between the peripheral seal 160 and annular seal 162 of the flexible overlay 144 and the closure base 142, hermetically seal the variable-volume storage chamber with respect to the ambient atmosphere, and fixedly secure the vial cap 127 onto the vial body 112.

In the illustrated embodiment, the flexible closure overlay 144 defines the flexible base and sealing member 146, the penetrable and resealable portion or septum 148, the valve cover or member 150 of the one-way valve 118, and the approximately dome-shaped spring 152. The closure base 142 defines, within the circular-shaped recess 156, the valve-receiving recess 164 aligned, e.g., axially, with the one-way valve 118, and at least one fluid-flow aperture 190 within the valve-receiving recess 164.

Similar to the embodiments described above in connection with FIGS. 1-7, the penetrable and resealable portion or septum 148 is penetrable by a needle, filling or injection member (not shown) for sterile or aseptically filling the storage chamber 114 with multiple doses of the substance to be dispensed. The septum 148, can be formed of a material that is sufficiently elastic to close itself after withdrawal of the needle, filling or injection member therefrom to thereby ensure that the head loss left by a residual penetration hole after the injection member is withdrawn prevents fluid ingress therethrough. Although such a septum 148 is self-closing, the septum may be resealed by a liquid sealant, such as silicone or a silicone-based sealant, and/or the application of radiation or energy thereto to hermetically seal the substance within the storage chamber 114 from the ambient atmosphere and thereby maintain the sterility of the substance. The septum 148 may be penetrable for sterile filling the variable-volume storage chamber and resealable, such as by the application of laser, other radiation, or thermal energy, to hermetically seal the filled substance within the storage chamber in accordance with the teachings of any of the patents and patent applications incorporated by reference above. Alternatively, the septum 148 may be penetrable for sterile filling the variable-volume storage chamber, and resealable with a liquid sealant, such as a silicone sealant, to hermetically seal the filled substance within the storage chamber, in accordance with the teachings of any of the patents and patent applications incorporated by reference above.

Prior to filling the variable-volume storage chamber, the sealed empty chamber may be sterilized by injecting a fluid sterilant therein, such as nitric oxide, with a needle, filling or injection member through the penetrable and resealable portion 148, and the needle employed for injecting the fluid sterilant and/or the substance to be sterile filled into the variable-volume storage chamber may be a self opening and closing needle, in accordance with the teachings of any of the patents and patent applications incorporated by reference above.

Similar to the embodiments described above, the one-way valve 118 includes a relatively rigid valve seat 170 that is received within the flexible valve member or cover 150 and defines a normally closed, valve seam 172 therebetween. The valve member 150 engages, and in alternative embodiments forms an interference fit with, the valve seat 170 to thereby form a fluid-tight seal in the normally closed position and, in turn, maintain the substance within the storage chamber 114 in a sterile and hermetically sealed condition. The valve 118 defines a valve opening pressure, and remains in the normally closed position unless a pressure differential across the valve exceeds the valve opening pressure. When a pressure differential across the valve does exceed the valve opening pressure, the valve member 150 expands, e.g., radially, relative to or otherwise moves away from the valve seat 170 and opens the valve seam 172 therebetween.

The valve 118 includes a substantially dome-shaped spring 152 formed of a resilient and/or elastomeric material. Similar to the embodiment described above, the spring 152 permits the valve member 118 to move between an extended first position wherein the valve member 150 is fully received within the valve opening 136 of the connector 130, and a depressed second position wherein the valve member 150 is depressed or otherwise moved distally within the valve opening 136 and out of engagement with the connector 130. As can be seen, the dome-shaped spring 152 normally biases the valve 118 in the direction from the second position toward the first position.

When in the first position, the interior surface 174 forming the valve opening 136 engages the valve member 150 or otherwise substantially prevents radial expansion or opening of the valve member 150 relative to the valve seat 170, and thus prevents the valve 118 from opening. The annular valve seam 172 is closed. When in the second position, the valve member 150 is disengaged from the connector interior surface 174 with sufficient space around it so that the valve 118 is free to open (and open the valve seam 172) when a pressure differential across the valve 118 exceeds the valve opening pressure to, in turn, permit expansion of the valve member 150 relative to the valve seat 170 and thereby allow the flow of substance from the variable-volume storage chamber therethrough.

The flexible valve member 150 defines a base portion 176 that engages an inner end of the valve seat 170 to support the valve seat within the valve 118. The base portion 176 defines one or more valve inlet apertures 178 therethrough in fluid communication with the normally closed annular valve seam 172 to permit fluid flow from the variable-volume storage chamber 114 through the valve 118 when in the second position and the pressure differential across the valve exceeds the valve opening pressure. The outlet end of the valve seat 170 defines a plurality of angularly spaced protuberances 179 thereon that engage a syringe connector 84 of the syringe 20 but permit the flow of fluid therebetween (between the protuberances 179) in order to allow fluid flow through the valve 118 and into the syringe 20.

In order to dispense the substance from the vial, the syringe or other delivery device 20 is connected to the connector 130. When connected to the vial 110, the connector 84 of the syringe engages the valve seat 170 and displaces the valve 118 from the first position to the second position. When in the second position, and upon withdrawal of the plunger 82 of the syringe, a vacuum or partial vacuum is created within the barrel of the syringe 20 which, in turn, creates a pressure differential across the valve 118. When the pressure differential across the valve 118 exceeds the valve opening pressure, the valve seam 172 opens and the substance within the variable-volume storage chamber flows through the fluid flow aperture(s) 190 and subsequently through the valve inlet aperture(s) 178 and, in turn, through the valve seam 172 and into the barrel of the syringe 20. As substance is dispensed from the variable-volume storage chamber 114, suction forces exerted on the sliding seal 186 caused by the exit of the substance from the storage chamber 114 cause the seal to move or slide within the vial body 112 toward the one-way valve 118 to reduce the volume of the variable-volume storage chamber 114 by substantially the same volume of substance dispensed.

When withdrawal of the syringe plunger 82 is terminated, the pressure differential, if any, across the valve 118 decreases to less than the valve opening pressure, and the flow of substance from the variable-volume storage chamber 114 through the valve 118 is terminated. Upon disconnection of the syringe connector 84 from the vial connector 130, the dome-shaped spring 152 drives the valve from the second position toward the first position where the interior surface 174 of the connector engages the valve member 150 and further prevents the possibility of any fluid flow through the valve. When another dose of substance is needed from the vial, the same steps may be repeated. Thus, the interior of the valve and storage chamber can be maintained sterile, aseptic, and/or contamination free, as desired, throughout dispensing of dosages from the storage chamber, as explained in the embodiment described above.

In FIGS. 11-13B, another embodiment of the device is indicated generally by the reference numeral 210. The device 210 is substantially similar to the devices 10, 10' and 110 described above in connection with FIGS. 8-10, and therefore like reference numerals preceded by the numeral "2" are used to indicate like elements. For simplicity, the following description is directed to the differences in the variable-volume storage chamber 214 within the vial body 212.

Figure 11:
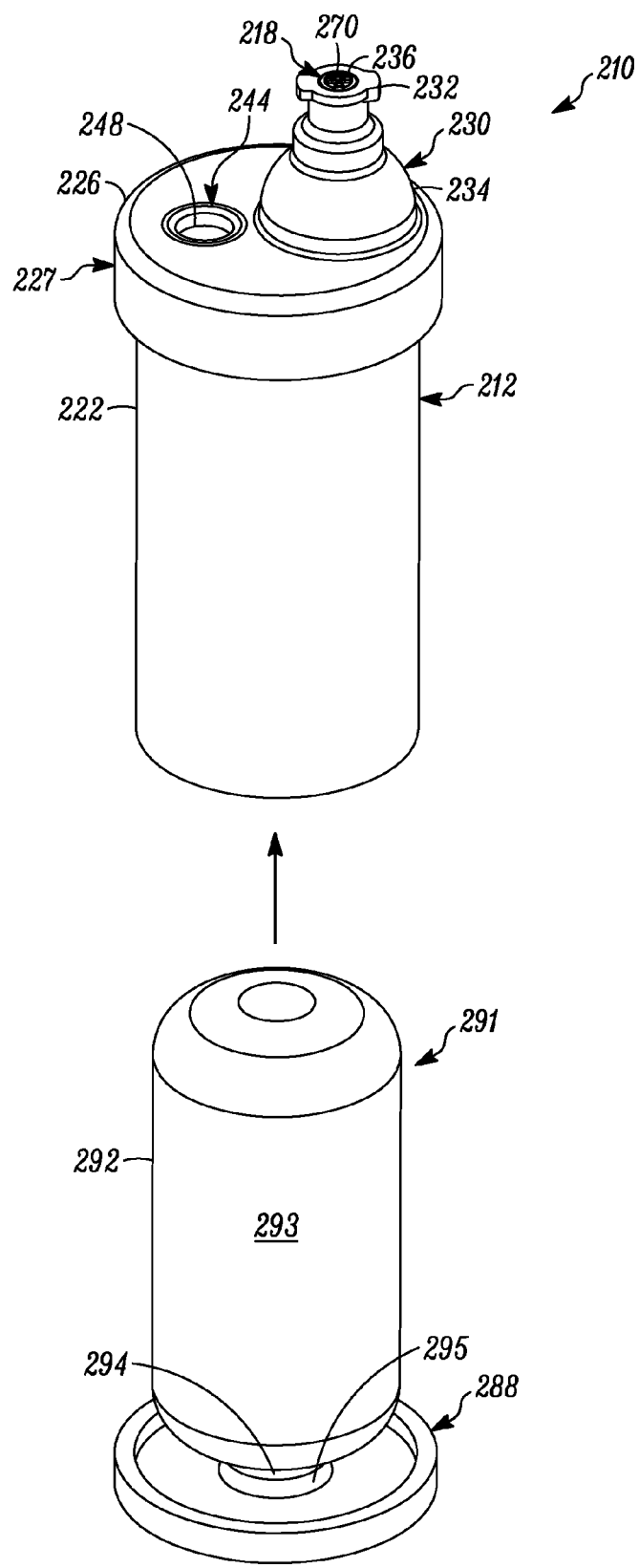
FIG. 11 is an exploded, perspective view of another embodiment of a multiple dose vial including a flexible bladder received within the vial body, and defining the variable-volume storage chamber between the flexible bladder wall and the side wall of the vial body.

As shown in the illustrated embodiment of FIG. 11, the vial 210 includes a collapsible flexible bladder 291 integrally formed with, and projecting from, a base closure 288. The base closure 288 sealingly encloses the base of the vial body 212, thereby sealing off the storage chamber 214 from the ambient atmosphere, and the flexible bladder 291 projects within the vial body 212 toward the opposing valve end of the vial 210. Alternatively, in other embodiments, the bladder 291 may extend from the closure 240 toward the base end of the vial 210. The variable-volume storage chamber 214 is defined between the flexible bladder 291 and the side wall 222 of the vial body 212. The flexible bladder 291 has a bladder wall 292 defining a bladder cavity 293 therein. The flexible bladder 291 has a substantially central opening 294 at a base end thereof, defining an open port 295 in the base closure 288 in fluid communication with the bladder cavity 293.

In the illustrated embodiment, the base closure 288 and a preform (not shown) for the flexible bladder 291 are injection molded, and the bladder 291 is, in turn, blow molded from the injection molded preform, in accordance with the teachings of any of the patents and patent applications incorporated by reference above. In other embodiments, the elastic bladder 291 is sealed and is compressible and expandable.

Figure 12B:
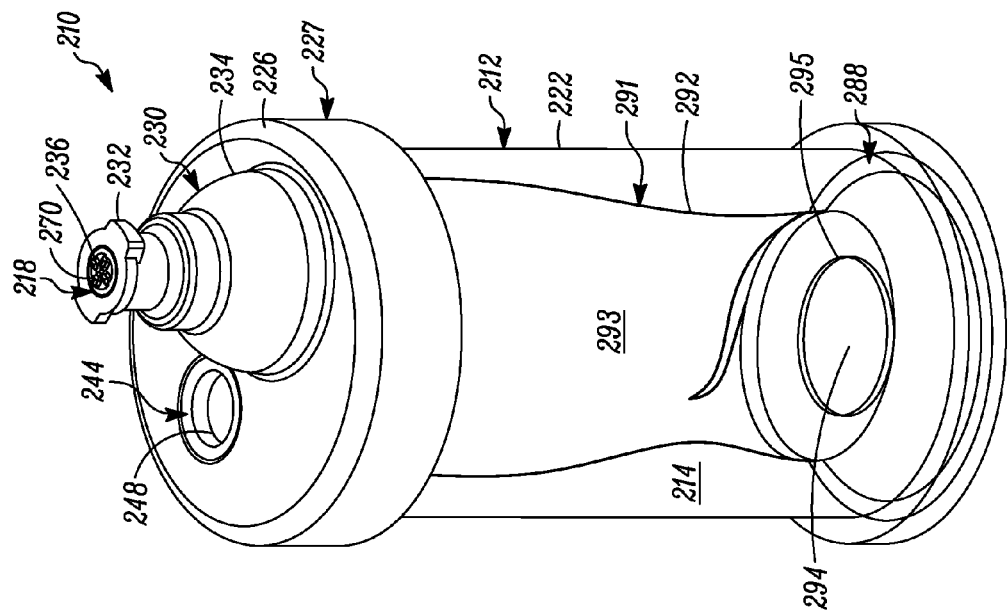
FIG. 12B is a top perspective view of multiple dose vial of FIG. 11, wherein the variable-volume storage chamber is partially filled and the flexible bladder is partially collapsed.
Figure 12A:
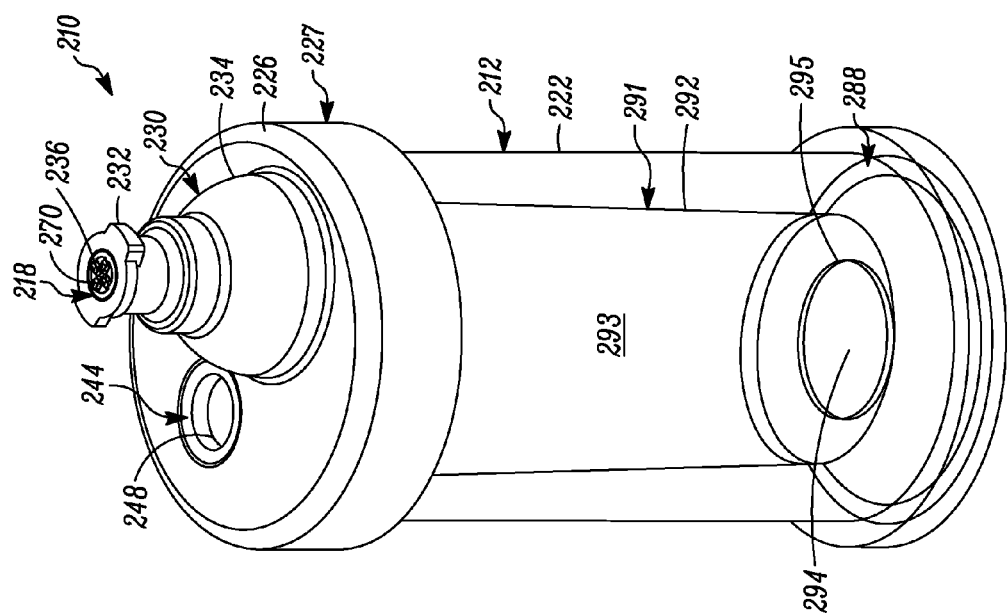
FIG. 12A is a top perspective view of the multiple dose vial of FIG. 11, wherein the bladder is in a fully expanded state and the variable-volume storage chamber is empty.
Figure 13B:
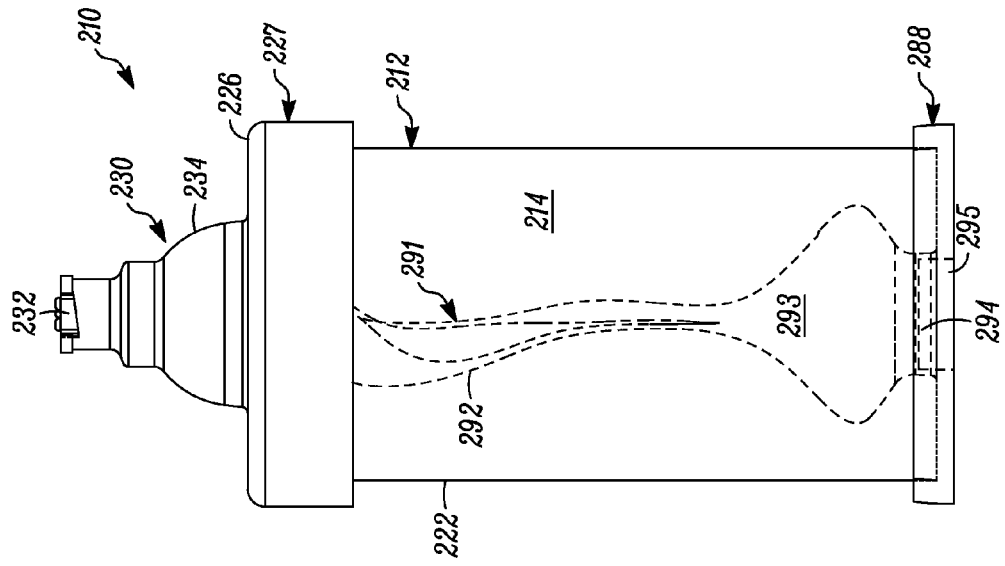
FIG. 13B is a side view of the multiple dose vial of FIG. 11, wherein the variable-volume storage chamber is filled and the flexible bladder is collapsed.
Figure 13A:
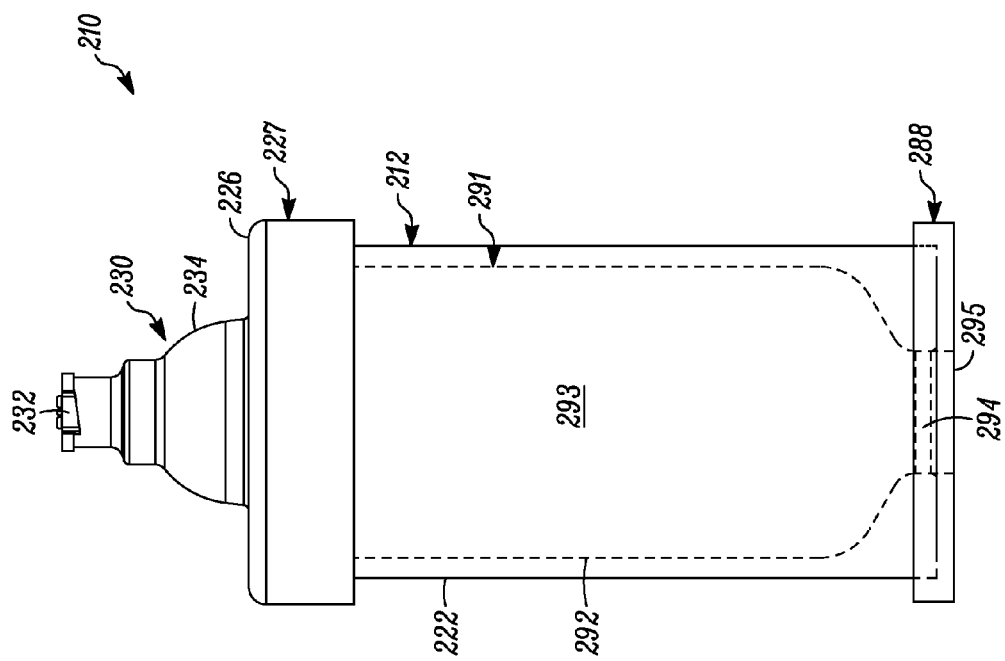
FIG. 13A is a side view of the multiple dose vial of FIG. 11, wherein the flexible bladder is fully expanded and the variable-volume storage chamber is empty.

The flexible bladder 291 is tubular in configuration and defines an external diameter dimensioned to fit within the vial body 212 when in the fully expanded state as shown in FIGS. 12A and 13A. However, the bladder 291 can have other configurations capable of performing the functions of the bladder as described herein. In the fully expanded state, as shown in FIGS. 11, 12A, 13A, the wall 292 of the bladder 291 defines a shape or morphology substantially the same as that of the vial body side wall 222 so that it conforms to and contacts the vial body side wall 222 throughout the interface of these two components. In this state, the empty variable-volume storage chamber is substantially airless.

The storage chamber 214 is sterile or aseptically filled with multiple doses of the substance to be dispensed via the penetrable and resealable portion or septum 248, in similar manner as in the embodiments described above. As the storage chamber 214 is filled with the substance, the bladder 291 collapses, as shown in FIGS. 12B and 13B and explained further below. Thereafter, when the connector 84 of the syringe 20 engages the valve seat 270, displaces the valve 218 from the first position to the second position, and the plunger 82 is subsequently withdrawn, the substance within the variable-volume storage chamber 214 flows through the one-way valve 218 and into the barrel of the syringe 20. As each dose of substance is dispensed from the variable-volume storage chamber 214, the bladder 291 inflates accordingly, as also explained further below. As shown in FIGS. 12A and 13A, the bladder 291 is expandable until the bladder wall 292 substantially conforms to the morphology of the side wall 222 of the vial body 212, to thereby eliminate any ullage or dead space and dispense substantially all of the substance in the storage chamber 214.

The sealed interior of the vial body 212, comprised of the variable-volume storage chamber 214 and the flexible bladder 291, defines a constant volume. As the volume of the storage chamber 214 increases, the volume of the flexible bladder cavity 293 substantially correspondingly decreases, and likewise, as the volume of the storage chamber 214 decreases, the volume of the flexible bladder cavity 293 substantially correspondingly increases.

As shown in FIG. 11, the flexible bladder 291 is assembled into the vial body 212 in its fully expanded state. Any air in the vial body 212 is thus displaced out the rear of the vial body 212 during assembly. Thereafter, when the sealed variable-volume storage chamber 214 is filled with a desired volume of substance, i.e., when substance is filled between the side wall 222 of the vial body 212 and the wall 292 of the flexible bladder 291, the flexible bladder 291 collapses accordingly, where a substantially equal volume of air flows out of the bladder cavity 293, through the open port 295, and into the ambient atmosphere. Afterwards, when a dose of the substance within the variable-volume storage chamber 214 is dispensed therefrom, through the valve 218, the pressure differential between the variable-volume storage chamber 214 and the atmosphere causes a substantially equal volume of air to flow into the bladder cavity 293, through the port 295, and re-expand the bladder. In some embodiments, a one-way valve is inserted into the open port 295 of the base closure 288 after the variable-volume storage chamber 214 is filled with the substance and the bladder 291 is collapsed. The one-way valve allows air to flow into the bladder cavity 293 with each dose of substance dispensed, but substantially prevents air from flowing out of the cavity. As may be recognized by those of ordinary skill in the pertinent art based on the teachings herein, the one-way valve may take the form of any of numerous different one-way valves, that are currently known, or that later become known, for performing the function of the one-way valve as described herein, including without limitation a check valve, a duckbill valve, a flapper valve or an umbrella valve.

Figure 14:
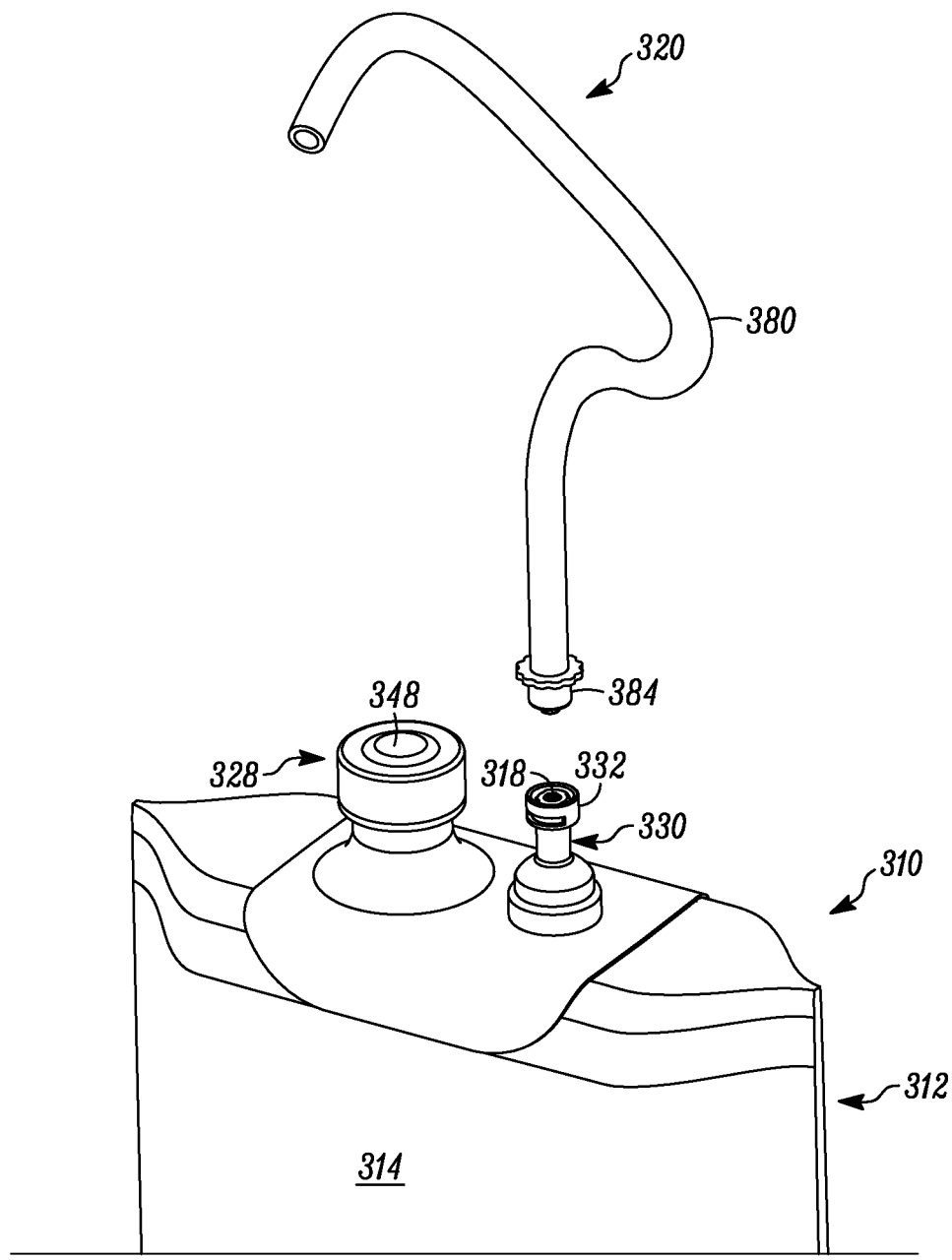
FIG. 14 is a partial top perspective view of another embodiment of a multiple dose vial, wherein the body is a flexible and collapsible pouch including an inlet filling port and an outlet connector, and also showing a flexible tube connectable to the connector for withdrawing one or more doses of the stored substance from the variable-volume storage chamber of the pouch.
Figure 15:
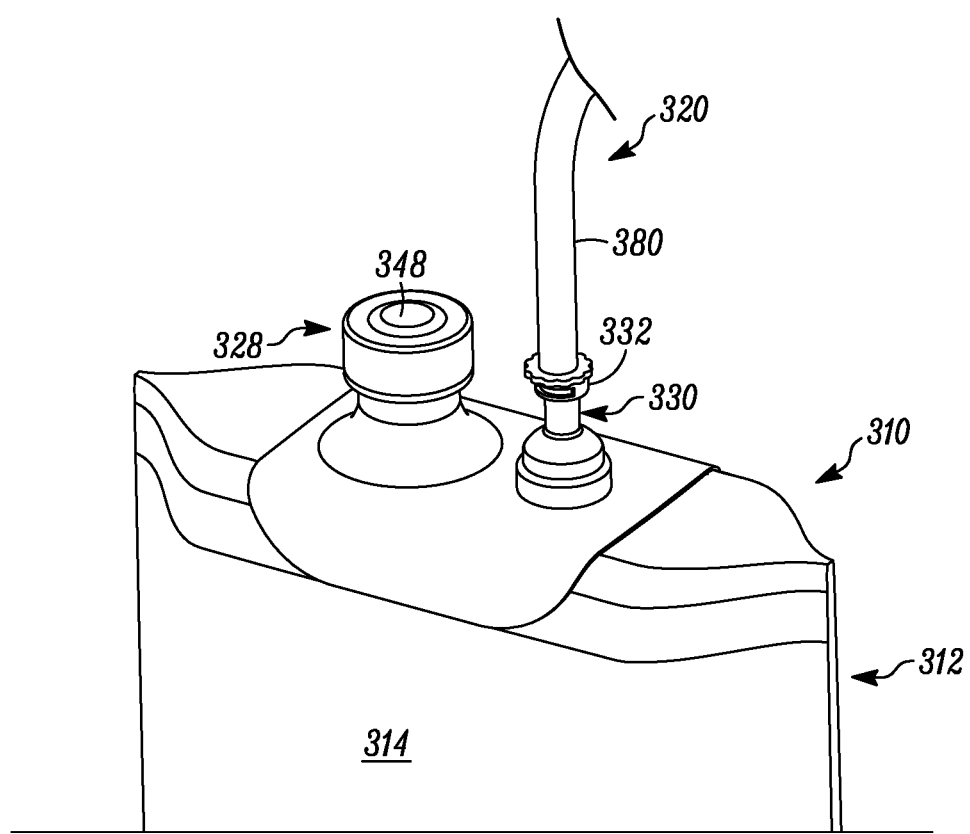
FIG. 15 is an enlarged partial top perspective view of the multiple dose vial of FIG. 14, illustrating the connector of the flexible tube fully engaged with the connector of the multiple dose vial, allowing one or more doses of the stored substance to be withdrawn from the storage chamber.
Figure 16:
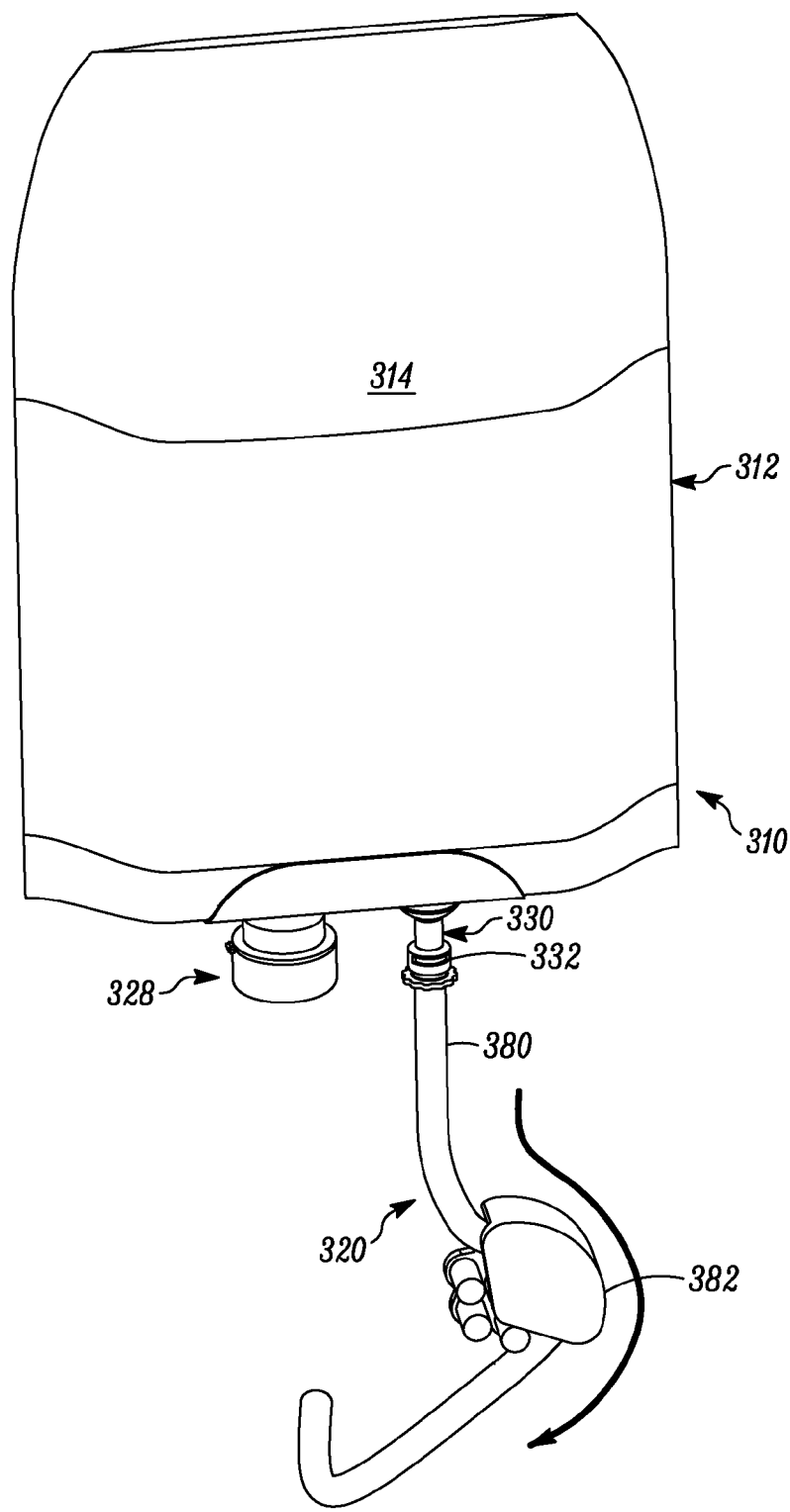
FIG. 16 is a side view of the multiple dose vial of FIG. 14 in an upside-down position, such as for hanging, illustrating the connector of the flexible tube fully engaged with the connector of the multiple dose vial and a pump operatively connected to the tube for creating a pressure differential greater than the valve opening pressure across the one-way valve.

In FIGS. 14-16, another device is indicated generally by the reference numeral 310. The device 310 is substantially similar to the devices 10, 10', 110 and 210 described above in connection with FIGS. 1-13B, and therefore like reference numerals preceded by the numeral "3" are used to indicate like elements. A primary difference of the device 310 in comparison to the device 10 is that the body 312 is a collapsible bladder, bag or pouch, rather than a rigid vial body 12, as hereinafter described.

The collapsible pouch 312 defines the variable-volume storage chamber 314 therein. As shown best in FIGS. 14 and 15, the collapsible pouch 312 includes a filling port 328 and an outlet connector 330. In the illustrated embodiment, the filling port 328 and the connector 330 are both located at one end of the pouch 312. However, as should be recognized by those of ordinary skill in the pertinent art, the filling port and connector may equally be located at opposing ends of the pouch 312. The filling port may also be on the pouch 312 itself. Similar to the embodiments described above, the filling port 328 is utilized for sterile or aseptically filling the storage chamber 314 therethrough with multiple doses of the substance to be dispensed, and the outlet connector 330 is utilized for dispensing doses of substance therefrom. With each dose of substance dispensed, the pouch 312 is collapsible by approximately the same volume.

Similar to the above-described embodiments, the particular filling port 328 shown includes a penetrable and resealable portion or septum 348. The septum 348 is penetrable by a needle, filling or injection member (not shown) for sterile or aseptically filling the storage chamber 314 with multiple doses of the substance to be dispensed. The septum 348, in some embodiments, is formed of a material that is sufficiently elastic to close itself after withdrawal of the needle, filling or injection member therefrom to thereby ensure that the head loss left by a residual penetration hole after the filling or injection member is withdrawn prevents liquid ingress therethrough. Like septums 48, 48', 148, 248, although the septum 348 is sufficiently self-closing to prevent liquid passage, the septum may be resealed by a liquid sealant, such as silicone or a silicone-based sealant, and/or the application of radiation or energy thereto in order to hermetically seal the substance within the storage chamber 314 to prevent ingress of air or contaminants from the ambient atmosphere or environment and thereby maintain the sterility thereof. The septum 348 may be penetrable for sterile filling the variable-volume storage chamber and resealable, such as by the application of radiation or energy, e.g., laser radiation or thermal energy, to hermetically seal the filled substance within the storage chamber in accordance with the teachings of any of the patents and patent applications incorporated by reference above. Alternatively, the septum 348 may be penetrable for sterile filling the variable-volume storage chamber 314, and resealable with a liquid sealant, such as a silicone sealant, to hermetically seal the filled substance within the storage chamber, in accordance with the teachings of any of the patents and patent applications incorporated by reference above.

The outlet connector 330 includes a one-way valve 318 therein, similar in design and function to the one way valves 18, 18', 118, and 218 of the above-described embodiments, and a Luer connector 332 formed at the outer end thereof. The one-way valve 318 is connectable in fluid communication with a syringe or other delivery device 320 via the Luer connector 332. As described above, the one-way valve 318 (i) permits substance from the storage chamber 314 to flow therethrough and into the dispensing member 320 when connected in fluid communication therewith, and (ii) substantially prevents any fluid flow in a substantially opposite direction therethrough and into the storage chamber 314 to thereby maintain the substance sterile, aseptic, and/or contamination free.

The illustrated delivery device 320 includes a flexible tube 380 having a connector 384 at an inlet end thereof, and a pump 382 (FIG. 16) operatively associated with the tube 380. In order to dispense the substance from the storage chamber 314 of the pouch 312, the connector 384 of the flexible tube 380 is connected to the pouch outlet connector 330 (FIGS. 15, 16). In the illustrated embodiment, the Luer connector 332 of the outlet connector 330 is a male Luer connector, and the flexible tube connector 384 is a female Luer connector. However, as may be recognized by those of ordinary skill in the pertinent art based on the teachings herein, any of numerous different connectors for either the delivery device or the pouch that are currently known, or that later become known, may be used.

When connected to the pouch 312, the connector 384 of the flexible tube 380 displaces the valve 318 from the first position to the second position, similarly to as described above with respect to the previous embodiments. When in the second position, operation of the pump 382 creates a pressure differential across the valve 318 exceeding the valve opening pressure, thereby opening the valve 318 and allowing the substance to flow from the storage chamber 314, through the valve 318, and through the tube 380.

Similar to as described above with respect to the previous embodiments, any ambient air or other fluid that could contaminate the interior of the valve 318 or storage chamber 314 is substantially prevented from flowing through the valve in the opposite direction. As a result, the interior of the valve and storage chamber can be maintained sterile, aseptic, and/or contamination free, as desired, throughout dispensing of dosages from the storage chamber. When operation of the pump 382 is terminated, the pressure differential, if any, across the valve 318 is less than the valve opening pressure, and the flow of substance from the variable-volume storage chamber 314 through the valve 318 is also terminated. Additionally, any substance within the flexible tube 380, between the valve 318 and the pump 382, is sealed by the pump 382, and prevented from flowing past it. As should be understood by those of ordinary skill in the pertinent art based on the teachings herein, any of numerous different pumps or actuators, currently known or that later become known, may be utilized with the flexible tube to draw fluid out of the storage chamber and through the one-way valve. For example, and without limitation, a peristaltic pump may be utilized. As another example, a syringe can be connected to the end of the tube 380 to withdraw fluid from the pouch 312.

As may be recognized by those of ordinary skill in the pertinent art based on the teachings herein, numerous changes and modifications may be made to the above-described and other embodiments of the present invention without departing from its scope as defined in the claims. For example, the components of the vial may be made of any of numerous different materials or combinations of materials that are currently known, or that later become known for performing the function(s) of each such component. Similarly, the components of the vial may take any of numerous different shapes and/or configurations, and may be manufactured in accordance with any of numerous different methods or techniques that are currently known, or later become known.

As another example, the penetrable and resealable portion may be located at a different part of the vial rather than the flexible closure overlay at the top end thereof. For example, and without limitation, in embodiments having a sliding seal or a flexible bladder formed with a base closure, the seal or the base closure may include the penetrable and resealable septum, respectively. In such a configuration, the variable-volume storage chamber may be filled in like manner as described above, but from the base end of a vial rather than from the opposing dispensing valve end. One advantage of such a configuration is that a sliding seal or base closure and flexible bladder including a penetrable and resealable septum would define a universal bottom which may be utilized with any vial having an open end at one end and a dispensing port and/or valve at the opposing end. Such a setup would require no modification to the vial. Rather, after assembling the sliding seal or base closure and flexible bladder in sealing engagement with the vial, it would be aseptically fillable via the septum therein, and define a variable-volume storage chamber resulting from the functionality of the sliding seal or the flexible bladder.

Further, rather than sterile or aspect fill the storage chamber with a penetrable and resealable septum, as described above, the storage chamber may be sterile or aseptic filled through a non-piercing filling cannula or probe that is connectable in fluid communication with a one-way valve mounted on the vial body or otherwise on the device, e.g., on the sliding seal or base closure, in fluid communication with the storage chamber. For example, the filling cannula and/or one-way valve may be constructed in accordance with the teachings of any of the following patents and patent applications, each of which is hereby expressly incorporated by reference in its entirety as part of the present disclosure: U.S. patent application Ser. No. 12/534,730, filed Aug. 3, 2009, entitled "Lyophilization Method and Device," now U.S. Pat. No. 8,272,411, which is a continuation of U.S. patent application Ser. No. 11/487,836, filed Jul. 17, 2006, entitled "Container with Valve Assembly and Apparatus and Method for Filling," now U.S. Pat. No. 7,568,509, which is a continuation of U.S. patent application Ser. No. 10/833,371, filed Apr. 28, 2004, entitled "Container with Valve Assembly for Filling and Dispensing Substances, and Apparatus and Method for Filling," now U.S. Pat. No. 7,077,176, which, in turn, claims the benefit of similarly titled U.S. Provisional Patent Application No. 60/465,992, filed Apr. 28, 2003, and U.S. Provisional Patent Application No. 60/469,677, filed May 12, 2003, entitled "Dispenser and Apparatus and Method for Filling a Dispenser," and similarly titled U.S. Provisional Patent Application No. 60/471,592, filed May 19, 2003; U.S. patent application Ser. No. 12/984,482, filed Jan. 4, 2011, entitled "Dispenser and Apparatus and Method for Filling a Dispenser," which is a continuation of similarly titled U.S. patent application Ser. No. 12/025,362, filed Feb. 4, 2008, now U.S. Pat. No. 7,861,750, which is a continuation of similarly titled U.S. patent application Ser. No. 11/349,873, filed Feb. 8, 2006, now U.S. Pat. No. 7,328,729, which is a continuation of similarly-titled U.S. patent application Ser. No. 10/843,902, filed May 12, 2004, now U.S. Pat. No. 6,997,219, which, in turn, claims the benefit of similarly titled U.S. Provisional Patent Application No. 60/469,677, filed May 12, 2003, and similarly titled U.S. Provisional Patent Application No. 60/471,592, filed May 19, 2003, and U.S. Provisional Patent Application No. 60/488,355, filed Jul. 17, 2003, entitled "Piston-Type Dispenser with One-Way Valve for Storing and Dispensing Metered Amounts of Substances, and Pivoting Cover for Covering Dispensing Portion Thereof," and U.S. Provisional Patent Application No. 60/539,814, filed Jan. 27, 2004, entitled "Piston-Type Dispenser with One-Way Valve for Storing and Dispensing Metered Amounts of Substances;" and U.S. patent application Ser. No. 12/724,370, filed Mar. 15, 2010, entitled "Method for Delivering a Substance to an Eye," which is a continuation of U.S. patent application Ser. No. 10/990,164, filed Nov. 15, 2004, entitled "Delivery Device and Method of Delivery," now U.S. Pat. No. 7,678,089, which, in turn, claims the benefit of similarly titled U.S. Provisional Patent Application No. 60/519,961, filed Nov. 14, 2003.

Alternatively, the storage chamber may be filled via a connector. For example, a sterile or aseptic connector may be constructed in accordance with the teachings of any of the following patents and patent applications, each of which is hereby expressly incorporated by reference in its entirety as part of the present disclosure: U.S. Provisional Patent Application No. 61/625,663, filed Apr. 17, 2012, entitled "Self Closing Connector," similarly titled U.S. Provisional Patent Application No. 61/635,258, filed Apr. 18, 2012; U.S. Provisional Patent Application No. 61/641,248, filed May 1, 2012, entitled "Device for Connecting or Filling and Method;" and U.S. patent application Ser. No. 13/080,537, filed Apr. 5, 2011, entitled "Aseptic Connector with Deflectable Ring of Concern and Method," which, in turn, claims the benefit of similarly titled U.S. Provisional Patent Application No. 61/320,857, filed Apr. 5, 2010.

The vial or other device embodying the present invention also may be used to store and dispense any of numerous different types of fluids or other substances for any of numerous different applications that are currently known, or later become known. In addition, the storage chamber need not be a variable-volume storage chamber. For example, in another embodiment, the storage chamber defines a substantially fixed volume, but includes a sterile filter, such as a micro-filter of a type known to those of ordinary skill in the pertinent art, that is coupled in fluid communication between the storage chamber and ambient atmosphere to allow air to flow into the storage chamber, but that sterilizes any such air that flows therethrough in order to maintain the interior of the variable-volume storage chamber sterile. Accordingly, this detailed description of embodiments is to be taken in an illustrative, as opposed to a limiting sense.

What is claimed is:

1. A device for storing multiple doses of a substance to be dispensed into one or more syringes or other delivery devices, comprising:
    a body;
    a storage chamber within the body for storing multiple doses of the substance therein; and
    a one-way valve connectable in fluid communication with a syringe or other delivery device and configured to allow fluid to flow in one direction therethrough but prevent ingress of fluid in an opposite direction, the one-way valve including a valve seat and a valve member normally engaging the valve seat to define a closed position, the valve member being movable relative to the valve seat when a pressure differential across the one-way valve exceeds a valve-opening pressure thereof to define an open position;
    wherein the valve seat and valve member are moveable together relative to a surface of the device between first and second positions;
    wherein, when in the first position, the surface of the device contacts the valve member and prevents the valve member from moving relative to the valve seat from the closed position to the open position, thereby preventing the one-way valve from opening into the open position, so that substance cannot pass through the one-way valve at any time in the first position, and when in the second position the valve member is sufficiently spaced from the surface of the device to permit movement of the valve member relative to the valve seat from the closed position to the open position when a pressure differential is generated across the valve that exceeds the valve opening pressure, so that substance from the storage chamber may flow through the one-way valve and into the syringe or other delivery device connected in fluid communication therewith.

2. A device as defined in claim 1, wherein the storage chamber comprises a variable-volume storage chamber.

3. A device as defined in claim 1, wherein the valve member defines an elastic valve member defining with the valve seat a normally closed valve seam that defines the closed position preventing the passage of fluid therethrough when a pressure differential across the valve is less than the valve opening pressure.

4. A device as defined in claim 3, wherein one or more of (i) the elastic valve member defines a progressively decreasing wall thickness in a direction from an inlet toward an outlet of the valve seam, or (ii) the valve seat defines a progressively increasing width or diameter in a direction from an inlet toward an outlet of the valve seam.

5. A device as defined in claim 1, wherein the device includes a penetrable and resealable portion that is penetrable by a needle, filling or injection member for filling the storage chamber with substance to be dispensed, and is resealable to hermetically seal a resulting penetration aperture in the portion.

6. A device as defined in claim 5, wherein the penetrable and resealable portion is resealable by one or more of a liquid sealant or the application of radiation or energy thereto.

7. A device as defined in claim 1, further comprising a connector located downstream of an outlet of the one-way valve, wherein the connector is adapted to connect thereto the syringe or other delivery device.

8. A device as defined in claim 7, wherein the connector is a Luer connector.

9. A device as defined in claim 1, wherein the one-way valve is normally biased in a direction from the second position toward the first position.

10. A device as defined in claim 9, further including a spring that normally biases the one-way valve in a direction from the second position toward the first position.

11. A device as defined in claim 10, wherein the spring is approximately dome shaped.

12. A device as defined in claim 1, wherein the surface of the device extends substantially annularly about the valve member.

13. A device as defined in claim 1, further comprising a connector located downstream of an outlet of the one-way valve, wherein the connector is adapted to connect thereto the syringe or other delivery device, and connection of the syringe or other delivery device causes the valve seat and valve member to move in a direction from the first position to the second position.

14. A device as defined in claim 13, wherein the connector defines the surface of the device in the first position.

15. A device as defined in claim 13, wherein the valve seat is configured so that the syringe or other delivery device engages the valve seat when connected to the device and moves the valve seat and valve member in a direction from the first position toward the second position.

16. A device as defined in claim 13, wherein the connector is a Luer connector.

17. A device as defined in claim 16, wherein the connector is a male or female Luer connector adapted to connect to a respectively corresponding female or male Luer connector of the syringe or other delivery device.

18. A device as defined in claim 17, wherein the Luer connector is either a threaded or slip fit Luer connector.

19. A device as defined in claim 1, wherein the storage chamber is hermetically sealed with respect to ambient atmosphere.

20. A device as defined in claim 19, wherein the storage chamber is (i) empty and sterile, or (ii) sterile and includes therein sterile or aseptic substance.

21. A device as defined in claim 20, wherein the substance is one or more of a medicament, pharmaceutical, vaccine, liquid nutrition product or supplement.

22. A device as defined in claim 2, wherein the body is a flexible and collapsible body and defines the variable-volume storage chamber therein.

23. A device as defined in claim 2, wherein the body is substantially rigid and the variable-volume storage chamber is defined by a flexible bladder received within the rigid body.

24. A device as defined in claim 23, wherein the flexible bladder is a pouch and defines the variable-volume storage chamber therein.

25. A device as defined in claim 1, further including a closure connected to the body and hermetically sealing the storage chamber with respect to ambient atmosphere.

26. A device as defined in claim 25, wherein the closure includes the one-way valve.

27. A device as defined in claim 26, wherein the closure further includes a connector adapted to connect thereto the syringe or other delivery device, and the one-way valve is received within the connector.

28. A device as defined in claim 27, wherein one or more of the connector or closure defines the surface of the device.

29. A device as defined in claim 28, wherein the one-way valve is normally biased in a direction from the second position toward the first position.

30. A device as defined in claim 29, further including a spring that normally biases the one-way valve in the direction from the second position toward the first position.

31. A device as defined in claim 30, wherein the spring is substantially dome shaped.

32. A device as defined in claim 25, wherein the closure includes a penetrable and resealable portion that is penetrable by a needle, filling or injection member for filling the storage chamber with substance, and is resealable to hermetically seal a resulting penetration aperture in the portion.

33. A device as defined in claim 32, wherein the closure includes a base, and a relatively flexible closure overlay mounted to the base and forming one or more of the penetrable and resealable portion or the one-way valve.

34. A device as defined in claim 33, wherein the flexible closure overlay forms the penetrable and resealable portion, the valve member, and an elastic spring that both allows the valve member to move between the first and the second positions and biases the valve member in the direction from the second position toward the first position.

35. A device as defined in claim 34, wherein the flexible closure overlay is located between the closure base and the body and forms a fluid-tight seal therebetween.

36. A device as defined in claim 33, wherein the variable-volume storage chamber is defined by a pouch formed integral with the closure base and projecting therefrom.

37. A device as defined in claim 36, wherein the pouch is blow molded from a preform defined at least in part by the closure.

38. A device for storing multiple doses of a substance to be dispensed into one or more syringes or other delivery devices, comprising:
   first means for storing therein multiple doses of the substance;
   second means comprising a valve seat and a valve member for coupling in fluid communication with a syringe or other delivery device, for allowing substance to flow in one direction therethrough and preventing ingress of substance in an opposite direction, and for moving the valve seat and valve member together between first and second positions relative to a third means; and
   the third means for contacting the valve member in the first position and thereby preventing the valve member from moving relative to the valve seat, thereby preventing the second means from opening into an open position, so that substance cannot pass through the second means, and for being spaced from the second means in the second position and thereby permitting the valve member to move relative to the valve seat, thereby permitting the second means to open into the open position when a pressure differential is generated across the second means exceeding an opening pressure of the second means, so that substance from the first means may flow through the second means and into the syringe or other delivery device connected in fluid communication therewith.

39. A device as defined in claim 38, further including fourth means for penetrating with a needle, filling or injection member and for sterile or aseptic filling the substance into the first means.

40. A device as defined in claim 39, wherein the fourth means comprises a penetrable and resealable portion.

41. A device as defined in claim 38, further comprising fifth means for connecting thereto the syringe or other delivery device.

42. A device as defined in claim 41, further comprising sixth means for biasing the second means in a direction from the second position toward the first position.

43. A device as defined in claim 42, wherein the first means is a storage chamber, the fifth means is a connector, the sixth means is a spring, and the third means is a surface of one or more of a body of the device or the connector that is engageable with the valve member in the first position.

44. A device as defined in claim 1, wherein the body includes a sliding seal received therein and spaced relative to the one-way valve, wherein the storage chamber is a variable-volume storage chamber defined within the body between the sliding seal and the one-way valve.

45. A device as defined in claim 44, wherein the sliding seal includes a penetrable and resealable portion that is penetrable by a needle, filling, or injection member for filling the variable-volume storage chamber with substance, and resealable to hermetically seal a resulting penetration aperture in the portion.

46. A device as defined in claim 45, wherein the penetrable and resealable portion is resealable by one or more of a liquid sealant or the application of radiation or energy thereto.

47. A device as defined in claim 1, further comprising a base closure sealingly enclosing the body at an opposite side of the body from the one-way valve, and a flexible bladder integrally formed with the base closure and projecting therefrom toward the one-way valve, wherein the storage chamber is a variable-volume storage chamber defined between the flexible bladder and the body.

48. A device as defined in claim 47, wherein the flexible bladder is configured to collapse when the variable-volume storage chamber is filled and expand when substance is dispensed from the variable-volume storage chamber.

49. A device as defined in claim 47, wherein the flexible bladder is blow molded from a preform defined at least in part by the base closure.

50. A device as defined in claim 47, wherein the base closure further includes a penetrable and resealable portion that is penetrable by a needle, filling or injection member for filling the variable-volume storage chamber with substance, and resealable to hermetically seal a resulting penetration aperture in the portion.

51. A device as defined in claim 50, wherein the penetrable and resealable portion is resealable by one or more of a liquid sealant or the application of radiation or energy thereto.

52. A method comprising the following steps:
   i. storing multiple doses of a substance to be dispensed in a storage chamber of a device, the device comprising a body, the storage chamber within the body for storing multiple doses of the substance therein, and a one-way valve connectable in fluid communication with a syringe or other delivery device and configured to allow fluid to flow in one direction therethrough but prevent ingress of fluid in an opposite direction, the one-way valve including a valve seat and a valve member normally engaging the valve seat to define a closed position, the valve member being movable relative to the valve seat when a pressure differential across the one-way valve exceeds a valve-opening pressure thereof to define an open position, wherein the valve seat and valve member are moveable together relative to a surface of the device between first and second positions, wherein, when in the first position a surface of the device contacts the valve member and prevents the valve member from opening into the open position, so that substance cannot pass through the one-way valve at any time in the first position, and when in the second position the one-way valve is sufficiently spaced from the surface of the device to permit movement of the valve member relative to the valve seat from the closed position to the open position when a pressure differential is generated across the valve that exceeds the valve opening pressure, so that substance from the storage chamber may flow through the one-way valve and into the syringe or other delivery device connected in fluid communication therewith; and sealing the stored multiple doses with respect to ambient atmosphere;
   ii. connecting a syringe or other delivery device in fluid communication with the one-way valve in fluid communication with the storage chamber;
   iii. dispensing a dose of substance from the storage chamber through the one-way valve and into the syringe or other delivery device;
   iv. preventing ambient fluid from passing through the one-way valve and into the storage chamber during step iii; and
   v. repeating steps ii through iv with the same multiple dose device.

53. A method as defined in claim 52, wherein step (iii) includes creating at least a partial vacuum in the syringe or other delivery device and creating a pressure differential across the one-way valve that exceeds a valve opening pressure thereof.

54. A method as defined in claim 52, further including during or after step (ii), moving the valve seat and valve member from (i) the first position to (ii) the second position.

55. A method as defined in claim 54, wherein the moving step includes engaging the one-way valve with the syringe or other delivery device.

56. A method as defined in claim 52, further comprising maintaining the substance in the storage chamber hermetically sealed with respect to ambient atmosphere throughout at least steps (i) through (iv).

57. A method as defined in claim 56, further comprising maintaining the substance in the storage chamber sterile or aseptic at least throughout steps (i) through (iv).

58. A device as defined in claim 1, wherein the one-way valve is configured to be engaged by a syringe or other delivery device to move the valve seat and valve member from the first position to the second position and receive substance from the storage chamber and through the one-way valve into said syringe or other delivery device.

* * * * *

UNITED STATES PATENT AND TRADEMARK OFFICE
CERTIFICATE OF CORRECTION

PATENT NO. : 9,801,787 B2  
APPLICATION NO. : 13/744379  
DATED : October 31, 2017  
INVENTOR(S) : Daniel Py Page 1 of 1

It is certified that error appears in the above-identified patent and that said Letters Patent is hereby corrected as shown below:

In the Claims

Claim 34, Column 25, Line 48, "member" should be deleted.

Claim 34, Column 25, Line 49, "member" should be deleted.

Signed and Sealed this  
Twentieth Day of February, 2018

Andrei Iancu  
*Director of the United States Patent and Trademark Office*